(12) United States Patent
Charbel et al.

(10) Patent No.: US 7,191,110 B1
(45) Date of Patent: Mar. 13, 2007

(54) PATIENT SPECIFIC CIRCULATION MODEL

(75) Inventors: Fady T. Charbel, River Forest, IL (US); Marlyn E. Clark, Urbana, IL (US); Lewis Sadler, Fort Collins, CO (US); Noam Alperin, Chicago, IL (US); Francis Loth, Downers Grove, IL (US); Meide Zhao, Chicago, IL (US)

(73) Assignee: University of Illinois, Board of Trustees, Chicago, IL (US)

( * ) Notice: Subject to any disclaimer, the term of this patent is extended or adjusted under 35 U.S.C. 154(b) by 0 days.

(21) Appl. No.: 09/400,365

(22) Filed: Sep. 20, 1999

Related U.S. Application Data

(63) Continuation of application No. 09/243,870, filed on Feb. 3, 1999, now abandoned.

(60) Provisional application No. 60/073,580, filed on Feb. 3, 1998.

(51) Int. Cl.
G06G 7/48 (2006.01)
G09B 23/28 (2006.01)

(52) U.S. Cl. .................. 703/11; 703/2; 703/6; 434/262; 434/268; 434/270

(58) Field of Classification Search .................. 703/11, 703/2, 6; 434/262, 268, 270
See application file for complete search history.

(56) References Cited

U.S. PATENT DOCUMENTS 3,802,096 A * 4/1974 Matern ........................ 434/270
5,680,590 A * 10/1997 Parti ............................. 703/2
6,117,087 A * 9/2000 Kamm et al. ................ 600/504

OTHER PUBLICATIONS

Karplus, W. et al. "Simulation and Visualization of the Fluid Flow Field in Aneurysms: A Virtual Environments Methodology," Proc. of 7th Int'l Symp. of Micro Machine and Human Science, Oct. 1996, pp. 35-41.*
Foutrakis, G. "Finite Element Modeling of Intracranial Arterial Blood Flow and Saccular Aneurysm Formation," 1994 [retrieved on Jun. 5, 2000]. Retrieved from the Internet: <URL: neuronet.pitt.edu/~georgef/fem.html>.*
Foutrakis, G. "Efficient Segmentation and 3-D Resonstruction of Complex Vascular Structures from Magnetic Resonance Angiography Imaging Data," 1994 [retrieved on Jun. 5, 2000]. Retrieved from the Internet: <URL: neuronet.pitt.edu/~georgef/mra_seg.html>.*
Foutrakis, G. "Construction of 3-D Intracranial Arterial Meshes from Magnetic Resonance Angiography," 1994 [retrieved on Jun. 5, 2000]. Retrieved from the Internet: <URL: neuronet.pitt.edu/~georgef/mra2mesh.html>.*

(Continued)

Primary Examiner—Hugh Jones
(74) Attorney, Agent, or Firm—Schwegman, Lundberg, Woessner & Kluth, P.A.

(57) ABSTRACT

A method and apparatus are provided for modeling circulation in a living subject. The method includes the steps of developing a model for living subjects in general and correcting the model to substantially conform to the overall cerebral physiology of the living subject. The method further includes the step of calculating a cerebral flow of the living subject based upon the corrected model and a selected cerebral blood flow perturbation.

30 Claims, 26 Drawing Sheets

OTHER PUBLICATIONS

Silipo, R. et al. "Dynamics Modelling in Brain Circulation," Proc. of 1997 IEEE Workshop in Neural Networks for Signal Processing, Sep. 1997, pp. 162-171.*

Ramalinga, S. et al. "Hemodynamics of Intravascular Lateral Aneurysms: Flow Siimulation Studies," Proc. of 1997 16th Southern Biomedical Engineering Conf., Apr. 1997, pp. 224-227.*

Wolk, S. et al. "Computer Simulation of Cerebrovascular Circulation and Assessment of Intracranial Hemodynamics during Induction of Anesthesia," Proc. of 1995 IEEE 21st Annual Northeast Bioengineering Conf., May 1995, pp. 95-96.*

Ortega, V. "Predicting Cerebral Aneurysms with CFD," Technical Engineering, vol. 119, No. 1, Jan. 1997, pp. 76-77.*

Hademenos, G. "The Biophysics of Stroke," American Scientist, vol. 85, No. 3, May-Jun. 1997, pp. 226-235.*

AnalyzeAVW—product overview, 1997 [retrieved on Jun. 5, 2000]. Retrieved from the Internet: <URL: www.mayo.edu/bir/analyzeavw/analyzeavw_new.html>.*

TCD Simulator—product overview, 1999 [retrieved on Jun. 5, 2000]. Retrieved from the Internet: <URL: www.hemodynamic.com>.*

J.R. Womersley, "Oscillatory Flow in Arteries: The Constrained Elastic Tube as a Model of Arterial Flow and Pulse Transmission", *Phys. in Med. & Biol.*, vol. 2, pp. 178-187 (1958).

Ling, et al., "A Nonlinear Analysis of Pulsatile Flow in Arteries", *J. Fluid Mech.*, vol. 55, part 3, pp. 493-511 and illustration facing p. 512 (1972).

Kufahl, et al., "A Circle of Willis Simulation Using Distensible Vessels and Pulsatile Flow", *Journal of Biomechanical Engineering*, vol. 107, pp. 112-122 (May 1985).

Clark, et al., "Natural and Surgically Imposed Anastomoses of the Circle of Willis", *Neurological Research*, vol. 11, pp. 217-230 (Dec. 1989).

Chao & Hwang, "Functional Dynamics of the Circle of Willis", 1972, T.I.T. *Journal of Life Sciences*, vol. 2, pp. 81-88.

Charbel, et al., abstract: "Predictive Value of a Computerized Model of the Cerebral Circulation", Oct. 1994, 44th Annual Meeting, Congress of Neurological Surgeons.

Charbel, et al., abstract: "Validation and Clinical Potential of a Computerized Model of the Cerebral Circulation", Jan. 1996, First Annual Meeting of the Joint Section on Cerebrovascular Surgery of the American Association of Neurological Surgeons and the Congress of Neurological Surgeons.

Charbel, et al., abstract: "Phase Contrast MR Flow Measurement System Using Volumetric Flow Constrainted Image Interpolation and Color Coded Image Visualization", Sep. 1997, 47th Annual Meeting, Congress of Neurological Surgeons.

Clark and Kufahl, "Simulation of the Cerebral Macrocirculation", from MIT Press, pp. 380-390 in *Cardiovascular System Dynamics* (Baan, et al., Editors).

Clark, et al., "Engineering Analysis of the Hemodynamics of the Circle of Willis", Aug. 1965, *Archives of Neurology*, vol. 13, pp. 173-182.

Clark, et al., "Simulation Studies of Factors Influencing the Cerebral Circulation", 1967, *Acta Neurol. Scandinav.*, vol. 43, pp. 189-204.

Duros, et al., "On the Rupture of an Aneurysm", May 1991, University of Illinois (Urbana) Dept. of Theoretical and Applied Mechanics.

Fukushima, et al., "Vortex Generation in Pulsatile Flow Through Arterial Bifurcation Models Including the Human Carotid Artery", Aug. 1988, *Transactions of the ASME*, vol. 110, pp. 166-171.

Helal, "Derivation of Closed-Form Expression for the Cerebral Circulation Models", 1994, *Comput. Biol. Med.*, vol. 24, pp. 103-117.

Hillen, et al., "A Mathematical Model of the Flow in the Posterior Communicating Arteries", 1982, *J. Biomechanics*, vol. 15, No. 6, pp. 441-448.

Hillen, et al., "A Mathematical Model of the Flow in the Circle of Willis", 1986, *J. Biomechanics*, vol. 19, No. 3, pp. 187-194.

Hillen, et al., "Analysis of Flow and Vascular Resistance in a Model of the Circle of Willis", 1988, *J. Biomechanics*, vol. 21, No. 10, pp. 807-814.

Himwich, et al., "The Circle of Willis as Simulated by an Engineering Model", Aug. 1965, *Arch. Neurol.*, vol. 13, pp. 164-172.

Himwich and Clark, "Simulation of Flow and Pressure Distributions in the Circle of Willis", 1974, *Pathology of Cerebral Microcirculation*, Berlin Symposium.

Imaeda and Goodman, "Analysis of Non-Linear Pulsatile Blood Flow in Arteries", 1980, *J. Biomechanics*, vol. 13, pp. 1007-1022.

Kufahl, Ph.D. thesis: "Numerical Solution of Unsteady Viscous Flow in Looping Arterial Networks", 1979, University of Illinois (Urbana) Graduate College, 392 pages plus abstract and table of contents.

Kufahl and Clark, "A Circle of Willis Simulation Using Distensible Vessels and Pulsatile Flow", May 1985, *Journal of Biomechanical Engineering*, vol. 107, pp. 112-122 and errata, p. 320 (Nov. 1985).

Leipsch and Moravec, "Pulsatile Flow of Non-Newtonian Fluid in Distensible Models of Human Arteries", 1984, *Biorheology*, vol. 21, pp. 571-586.

Ling and Atabek, "A Nonlinear Analysis of Pulsatile Flow in Arteries", 1972, *J. Fluid Mech.*, vol. 55, part 3, pp. 493-511.

Perktold, et al., "Pulsatile Non-Newtonian Blood Flow Simulation Through a Bifurcation with an Aneurysm", 1989, *Biorheology*, vol. 26, pp. 1011-1030.

Perktold and Peter, "Numerical 3D-Simulation of Pulsatile Wall Shear Stress n an Arterial T-Bifurcation Model", Sep. 1990, *J. Biomed. Eng.*, vol. 12, pp. 2-12.

Perktold, et al., "Pulsatile non-Newtonian Blood Flow in Three-Dimensional Carotid Bifurcation Models: A Numerical Study of Flow Phenomena Under Different Bifurcation Angles", Nov. 1991, *J. Biomed. Eng.*, vol. 13, pp. 507-515.

Perktold, et al., "Three-Dimensional Numerical Analysis of Pulsatile Flow and Wall Shear Stress in the Carotid Bifurcation", 1991, *J. Biomechanics*, vol. 24, No. 6, pp. 409-420.

Porenta, et al., "A Finite-Element Model of Blood Flow in Arteries Including Taper, Branches, and Obstructions", May 1986, *Journal of Biomechanical Engineering*, vol. 108, pp. 161-167.

Raines, et al., "A Computer Simulation of Arterial Dynamics in the Human Leg", 1974, *J. Biomechanics*, vol. 7, pp. 77-91.

Raines, et al., "A Computer Simulation of the Human Arterial System", 1975, Summer Computer Conference Proceedings.

Roller and Clark, "Precursor Cerebral Circulation Models", 1969, *J. Biomechanics*, vol. 2, pp. 241-250.

Walburn and Stein, "A Comparison of Steady and Pulsatile Flow in Symmetrically Branched Tubes", Feb. 1982, *Journal of Biomechanical Engineering*, vol. 104, pp. 66-68.

Wille, "Numerical Simulations of Steady Flow Inside a Three Dimensional Aortic Bifurcation Model", Jan. 1984, *J. Biomed. Eng.*, vol. 6, pp. 49-55.

Yung, et al., "Three-Dimensional Steady Flow Through a Bifurcation", May 1990, *Journal of Biomechanical Engineering*, vol. 112, pp. 189-197.

Charbel, F., et al., *Neurovascular flow simulation review*, 20 Neurological Research 107155 (Mar. 1998).

Segers, P., et al., *Assessment of distributed arterial network models*, Medical & Biological Engineering & Computing 729-736 (Nov. 1997).

Steinman, D.A., et al., *MR measurement and numerical simulation of steady flow in an end-to-side anastomosis model*, 29-4 J. Biochemica 537-542 (1996).

Sud, V.K., et al., *mathematical modelling of flow distribution in the human cardiovascular system*, 30 Medical & Biological Engineering & Computing 311-316 (1992).

Viedma, A., et al., *Extended Willis circle model to explain clinical observations in periorbital arterial flow*, 30-3 J. Biochemica 265-272 (1997).

Zagzoule, M., et al., *A global mathematical model of the cerebral circulation in man*, 19-12 J. Biochemica 1015-1022 (1986).

* cited by examiner

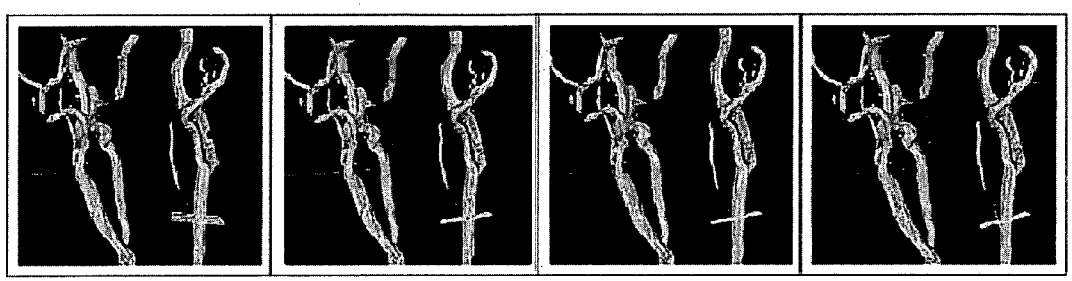
FIG. 19
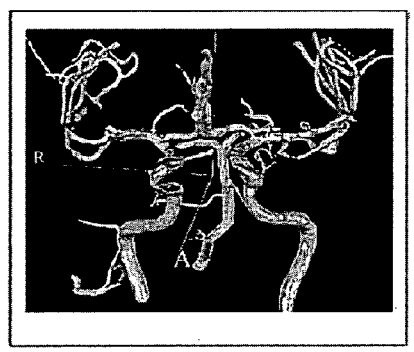 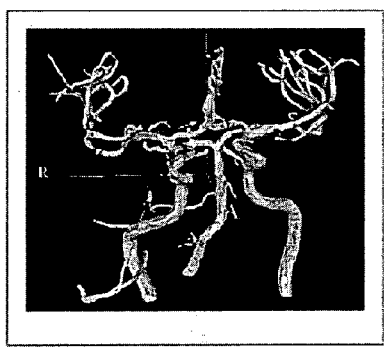
FIG. 20A    FIG. 20B

GENERIC 108-VESSEL
CARDIOVASCULAR MODEL

FINITE-DIFFERENCE SCHEME          RCR TERMINATION

PATIENT SPECIFIC CIRCULATION MODEL

This application is a continuation of U.S. patent application Ser. No. 09/243,870 filed Feb. 3, 1999, which is a continuation-in-part of U.S. provisional patent application Ser. No. 60/073,580 filed Feb. 3, 1998 (abandoned).

FIELD OF THE INVENTION

The field of the invention relates to blood circulation in the human body and more particularly, to blood flow within the human brain.

This application includes a microfiche appendix. The applicants have no objection to copying for patent purposes, but reserve all other rights whatsoever.

DESCRIPTION OF THE INVENTION

Stroke is a leading cause of death and disability in the United States, with significant socioeconomic impact. Therapeutic options for occlusive cerebrovascular diseases or trauma include a variety of reconstructive procedures such as endarterectomy, vessel transposition, bypass, angioplasty and thrombolysis; all of which share the common goal of enhancing the cerebral circulation.

However, because of the many individual variabilities between patients, assessment of the potential merit of such procedures is difficult and has mainly relied on clinical trials involving large groups of patients over long periods of time and at staggering costs (e.g., the NIH EC-IC bypass and carotid endarterectomy studies). The ethical dilemma of randomizing a patient to an ineffective or even harmful therapy not withstanding, selection of the optimal cerebral vascular reconstructive procedure in a given patient with complex occlusive patterns remains difficult and has to date relied on an intuitive process.

The ability to reliably simulate such procedures for any particular patient, increases the likelihood of selecting the optimal procedure. This invention applies a computerized model of the cerebral circulation to patients with cerebrovascular diseases to simulate any of a number of procedures, thereby providing a tool for selecting the optimal procedure for any given patient. The benefit of this invention provides improved patient outcome, significant cost savings and major impact on the way cerebrovascular reconstructive procedures are performed.

Charbel et al., $2^{nd}$ *International Skull Base Congress, $7^{th}$ Annual Meeting of the North American Skull Base Society*, (San Diego, July, 1996) discussed the applications of an earlier computerized model of the cerebral circulation in skullbase surgery. The role of computerized modeling in cerebrovasdular surgery was discussed by Charbel et al. at the $11^{th}$ *International Congress of Neurological Surgery* (Amsterdam, July 1997). Charbel et al. discussed the use of a computerized predictor for the tolerance of carotid artery sacrifice at $11^{th}$ *International Congress of Neurological Surgery* (Amsterdam, July 1997). Applications of modeling to cerebral revascularization are also contemplated.

SUMMARY

A method and apparatus are provided for modeling circulation in a living subject. The method includes the steps of developing a model for living subjects in general and correcting the model to substantially conform to the overall cerebral physiology of the living subject. The method further includes the step of calculating a cerebral flow of the living subject based upon the corrected model and a selected cerebral blood flow intervention (such as a bypass or carotid sacrifice).

BRIEF DESCRIPTION OF THE DRAWINGS

FIG. 19 depicts 3D surface renderings of a particular cut and three misalignment angles used by the system of FIG. 1;

FIG. 20 depicts a 3D localization of 4 particular intercranial arteries provided by the system of FIG. 1;

DETAILED DESCRIPTION OF AN ILLUSTRATED EMBODIMENT

Figure 1:
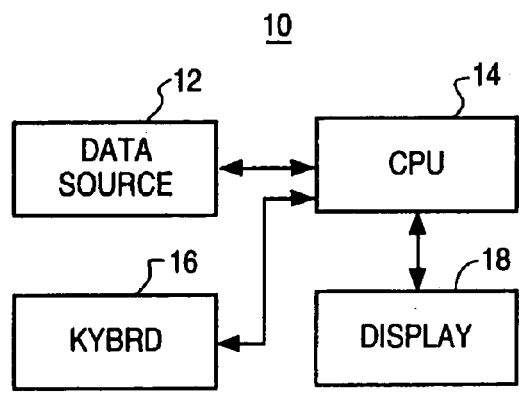
FIG. 1 is a block diagram of a modeling system for cerebral circulation in accordance with an illustrated embodiment of the invention.

The circulation around the "Circle of Willis" as first described in 1664 was initially thought to be a poorly functioning anastomotic network at the base of the brain. Willis, *Annals of Medical History* 2:81–94 (1940). Later it became accepted that it acts as the main distribution center for cerebral blood flow. In health, it distributes blood proportionately to each part of the brain; in disease, when the blood supply is decreased or diminished, it can redistribute flow in an effort to maintain cerebral hemodynamic homeostasis.

Because the cerebral circulation network is encased by the skull, it is very difficult to measure flow and pressure in its blood vessel constituents in a direct manner. Therefore computer simulation using the system 10 becomes an attractive way to predict flows and pressures in the cerebral circulation network. Fluid dynamic-based computer simulation offers the convenience of predicting pressures and flows at almost any desired section in the circulating system. Moreover, it not only can be used to estimate the flow and pressure under health and disease situations, but also can be used to predict the result of treatment procedures.

The simulation of cerebral circulation presents a range of challenging fluid dynamic problems, including: modeling the non-Newtonian properties of blood; dealing with "physiological" unsteady pulsatile flow; modeling the elasticity of vessel walls; and modeling moving boundaries caused by vessel wall elasticity. In addition, because the cerebral circulation network is an interconnected three-dimensional arterial network, the question arises of how the curvature of the artery is modeled. The asymmetric and three-dimensional characteristics of bifurcations are also very important issues.

Computer simulation started with models of the dog's cerebral circulation system. Clark et al., *Acta Neurol. Scandinav.*, 43:189–204 (1967), built a computer model for one-dimensional, linear, steady laminar flow and compared the result with an engineering model built by the same group [Himwich et al., *Archive of Neurology*, 13:164–172 (1965); Himwich et al., *Archive of Neurology*, 13:173–182 (1965)]. Cooper, *Ph.D. thesis*, Washington University (1970), studied the pulsatile flow effect. Chao & Hwang, *TiT Journal of Life Science*, 2:3–81 (1972) simulated non-linear pulsatile flow in their model. Himwich & Clark, *Pathology of Cerebral Microcirculation*, J. Cervos-Navarro, ed. (Walter de Gruyter, New York: 1974), pp. 140–152, and Clark & Kufahl, *Proc. of 1st Intl. Conf. Cardiovascular System Dynamics*, MIT Press (Boston, 1978), pp. 380–390, simulated the pulsatile flow in distensible vessels. Hillen et al., *J. Biomechanics*, 15:441–448 (1982), developed a non-linear, one-dimensional model, simplified to only five vessels, that accounted for pulsatile flow and elastic vessel walls. Kufahl & Clark, *J. Biomechanical Engineering*, 107:112–122 (1985), developed a one-dimensional finite-difference model with distensible vessels. Kufahl & Clark's dog model contained thirty-five vessels and allowed both steady flow and pulsatile flow to be studied.

Beginning in the late eighties, investigators began to simulate the human cerebral circulation. The process of adapting the animal models to generally simulate human cerebral circulation was not trivial.

The cerebral circulation network of a human is more complex than that of an animal. Considerations to be addressed included the number of arteries it was necessary to simulate, the selection of those arteries, and the configuration of the chosen arteries to represent the functionality of the Circle of Willis.

Cerebral circulation in humans is not consistent among individuals. The number of arteries, and parameters such as artery length and diameter differ from person to person, limiting the utility of standard data for individual cases. A successful model must be very flexible and robust to handle various simulation conditions.

The difficulty of obtaining direct measurements in humans limits the ability to accumulate parametric information and to refine the model.

Figure 2:
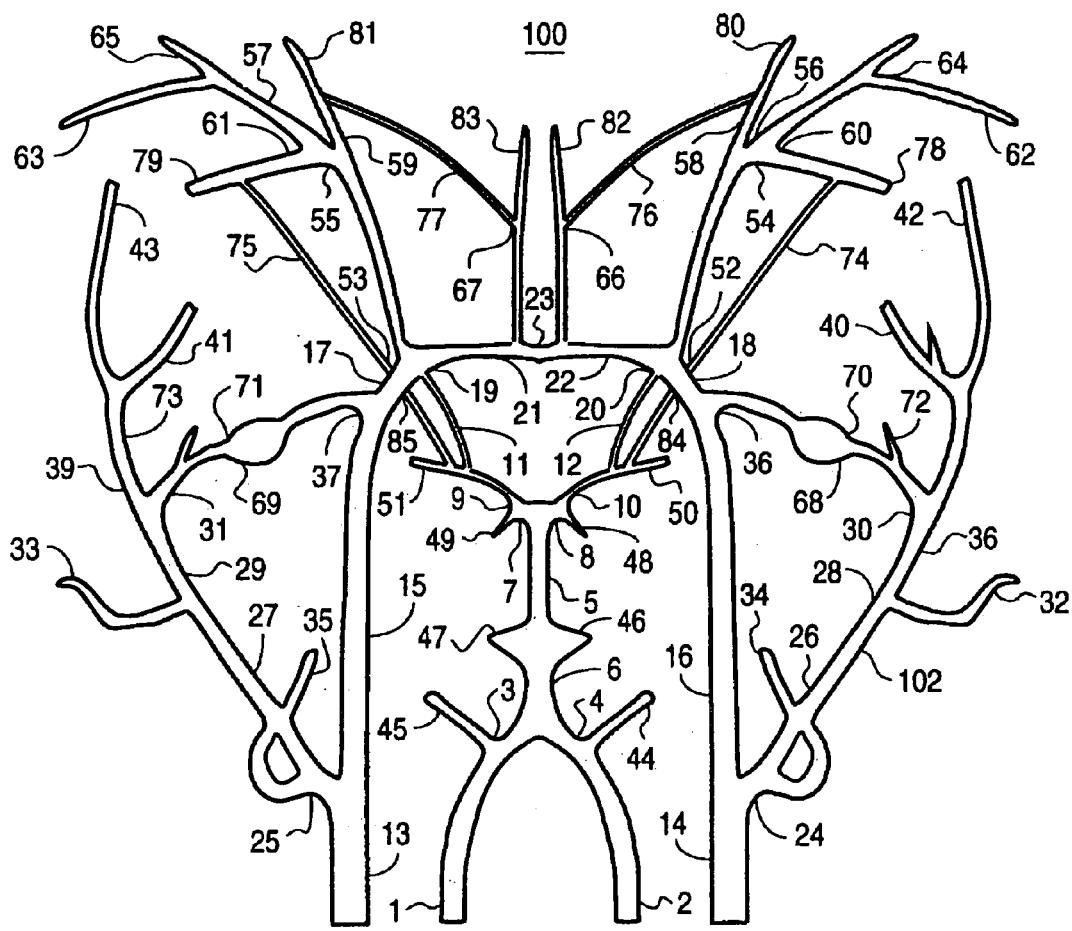
FIG. 2 is a cerebral circulation portion of the model used by the system of FIG. 1.

Clark et al., *Neurological Res.*, 11:217–230 (1989), developed an elaborate model for the human cerebral circulation network following the mathematical method used by Kufahl & Clark, *J. Biomechanical Engineering*, 107:112–122 (1985). The new model included seventy-three vessels representing the basic Circle of Willis. FIG. 2 is the schematic drawing of the 73 vessel model of Clark et al. After adding naturally occurring anastomoses, the total number of vessels increased to eighty-five. When artificial anastomoses were imposed, the number of vessels increased to eighty-seven.

Duros et al., *Neurological Res.*, 13:217–223 (1991), built a model that not only contained the cerebral arteries but also the human body main supply arteries. The Duros et al. model was used to simulate the rupture condition of aneurysm.

Beside the fluid dynamic models, several electrical models were built based on the similarity of the governing equations of electrical circuits and one-dimensional linear flow. Moreover, electrical networks are good at simulating networks with capacitance and resistance. Electrical network models are also well understood and provide convenient abstractions. Roller & Clark, *J. Biomechanics*, 2:244–251 (1969) simulated the pulsatile flow and flexible vessel wall using transmission line theory. Hillen, *Comput. Biol. Med.*, 24:103–118 (1994), built an electrical model using transmission line equations similar to the linearized Navier-Stokes equation and vessel wall deformation equation.

All existing cerebral circulation models are one-dimensional. All fluid dynamic-based models begin with the same set of governing equations, namely the one-dimensional continuity equation and Navier-Stokes equation. In those models, the following assumptions must be made in order to derive the equations [Long et al., *J. Fluid Mech.*, 55:493–511 (1972); Imaeda, *Ph.D. thesis*, Univ. of Waterloo (1975); Imaeda et al., *J. Biomechanics*, 13:1007–1021 (1980); Nerem et al., *Handbook of Engineering* (McGraw-Hill, New York: 1987), pp. 21.1–21.21]: (i) the flow is radially symmetric and includes well-developed laminar flow; (ii) blood is an incompressible, Newtonian fluid; and (iii) external forces (e.g., gravitational force) are negligible.

Because the most important components of interest are flow and pressure distributions, the one-dimensional integrated continuity and momentum equations are more convenient to use. The integrated governing equations are [Kufahl & Clark, *J. Biomechanical Engineering*, 107:112–122 (1985); Raines et al., *Proc. of the Summer Computer Simulation Conference* (MIT Press, Boston: 1975), pp. 890–900; Raines et al., *J. Biomechanics*, 7:77–91 (1974); Proenta et al., *J. Biomechanical Eng.*, 108:161–167 (1986)]:

continuity equation:

$$\frac{\partial Q}{\partial x} + \frac{\partial A}{\partial t} = 0 \quad (1)$$

momentum equation:

$$\frac{\partial Q}{\partial t} + \frac{\partial (Q^2/A)}{\partial x} = -\frac{A}{P}\frac{\partial P}{\partial x} + \frac{\pi D \tau}{\rho}, \quad (2)$$

where Q is a quantum flow and A is cross-sectional area. τ is the shear stress at the wall. The convective term contributes to the non-linearity of the governing equation set.

The main differences between the various models are how they define the problem (e.g., whether the flow is steady or pulsatile, whether the vessel wall is rigid or elastic, and whether a linear or non-linear governing equation is used to describe the flow field) and how they solve the problem (e.g. whether an analytical method or numerical method is used).

Even when the assumption is made that blood is Newtonian and flow is laminar, the governing equations are still non-linear because of the existence of the convective term in the momentum equation. Other non-linearities are included in the equation of state. For pipe flow, the convective term can be ignored because the gradient of the velocity is very small. The result is a linearized Navier-Stokes equation. If it is further assumed that the vessel wall is rigid and the flow is steady, the problem becomes Poiseuille flow, which can be solved analytically by applying the well-known Hagen-Poiseuille formula.

$$Q = \frac{\pi R^2 (P_a - P_b)}{8\mu l} \quad (3)$$

where R is the pipe radius and l is the pipe length.

For the rigid vessel unsteady pulsatile flow, Wormersley, *Phys. Med. Biology*, 2:178–187 (1957), provided an analytical solution for a single vessel. Ling & Attack, *J. Fluid Mech.*, 55:493–511 (1972), extended the Wormersley model by taking into account the consideration of non-linear effects and distensibility of the blood vessel. The finite-difference technique was employed to solve the problem numerically. To date, most existing numerical models can handle the non-linear, pulsatile flow and distensible vessel wall problem.

From the definition of the problem, computer modeling can be divided into two categories.

The first type of models applied the linear governing equation and rigid vessel assumption. For steady flow, the solution is given by the Hagen-Poiseuille formula. For unsteady flow, the solution is given by the Wormersley equations. Examples of models of this type include Clark et al. *Acta Neurol. Scandinav.*, 43:189–204 (1967), and Hillen et al., *J. Biomechanics*, 21:807–814 (1988). Because some of the electrical models [Roller and Clark, *J. Biomechanics*, 2:244–251 (1969); Hillen, *Comput. Bio. Med.*, 24:103–118 (1994)] were derived using the Hagen-Poiseuille formula as a model, they belong to this type. The advantages of a model with linear governing equation and rigid vessel assumptions is that the model is simple and an analytical solution exists. Thus, sensitivity analysis of parameters can be performed. It also offers the possibility of gaining insight into mechanisms that govern the flow in the cerebral network.

The other type is non-linear, pulsatile flow and distensible vessel models. Examples of models of this type include Kufahl & Clark [Kufahl and Clark, *J. Biomechanical Engineering*, 107:112–122 (1985); Clark et al., *Neurological Research*, 11:217–230 (1989); Kufahl, *Ph.D. thesis* (Univ. of Illinois, Urbana: 1980)] Hillen et al. [Hillen et al., *J. Biomechanics*, 15:441–448 (1982); Hillen et al., *J. Biomechanics*, 19:187–194 (1986)] and Duros et al., *Neurological Research*, 13:217–223 (1991).

The advantage of this kind of model is that the non-linear, pulsatile flow and distensible vessels are more accurate than the first type in describing the physical behavior of blood flow in arteries. For instance, Ling and Attack, *J. Fluid Mechanics*, 55:493–411 (1972), point out that the non-linear term cannot be neglected. Kufahl and Clark, *J. Biomechanical Engineering*, 107:112–122 (1985), showed that pulsatile flow resulted in a 10 percent increase of the total flow and contributed to some flow redistribution.

For the first type of problem, analytical solutions exist. For the second type of problem, numerical techniques must be used. The most commonly used computational fluid dynamics tools are finite-difference (FD), finite-element (FE) and finite volume (FV).

In the task of simulating the human cerebral circulation system, the finite-difference technique is widely used [Kufahl & Clark, *J. Biomechanical Engineering*, 107:112–122 (1985); Clark et al., *Neurological Research*, 111:217–230 (1989); Duros et al., *Neurological Research*, 13:217–223 (1991); Kufahl, *Ph.D. thesis* (Univ. of Illinois, Urbana, 1980)] because the application of finite-difference approach is straightforward and it can achieve certain accuracy with modest computational resources. However the finite-difference approach requires high regularity of the grid used, and this restrains the approach to be used in solving complex geometry problems.

In contrast, the finite-element approach can handle the complex geometry problem very easily, but the shortcoming of this method is that it needs much more computation time than the finite-difference method.

Cerebral network models usually contain hundreds of arteries and tens of bifurcations, which makes the use of the finite-element approach difficult using presently available computer equipment. To apply the finite element method in the network simulation, powerful computers are needed. With advances in computation technology, the finite-element method can be applied in cerebral network simulation. The present invention currently incorporates the finite-difference approach.

Stroke is a leading cause of death in the United States, as well as in most western countries. Among the many approaches available for cerebral revascularization (e.g., angioplasty, endarterectomy, bypass and embolectomy), the procedure of choice for each particular patient is, at least in theory, the one that restores cerebral blood flow. However because of the complex architecture of cerebral circulation, each patient has a unique dimensional structure. As a result, any surgical treatment can have different effects on different patients.

Computer models can simulate the cerebral circulation under "normal" conditions. Computer models can also be used to predict the results of potential treatment procedures. However, there is no other system currently available which forms a comprehensive model customized to the patient or which allows a user to perturb that model at will.

Hillen et al., *J. Biomechanics*, 15:441–448 (1982), built a non-linear one-dimensional model to study the functional significance of the Circle of Willis. The model consisted of two afferent and two efferent arteries connected by the posterior communicating artery. Hillen, et al. found that in normal cases, the flow in the posterior communicating artery was towards the posterior cerebral artery, and that the flow direction in posterior communicating artery depended on the ratio of peripheral resistance.

Kufahl and Clark, *J. Biomechanical Engineering*, 107: 112–122 (1985), developed a 35-vessel computer model for dog circulation. The model was non-linear, one-dimensional with pulsatile flow and distensible vessel walls. The computer simulation revealed the large drop in pressure over the length of the middle cerebral due to the large fluid friction at the vessel wall. Large pulses of flow were found in the common carotid but smaller pulses occurred farther downstream.

The comparison by Kufahl and Clark of running the model with steady flow versus pulsatile flow showed that the total flow rate increased because of the pulsatile flow. Kufahl and Clark also found flow redistribution in some arteries.

A series of stenoses were simulated by Kufahl and Clark to study the efficacy of the Circle of Willis in maintaining the flow under arterial disease. The middle cerebral flow was found to be well-maintained under different cases.

Hillen et al., *J. Biomechanics*, 21:807–814 (1988), extended their previous model [Hillen et al., *J. Biomechanics* 15:441–448 (1982)] to include 18 vessels. The effect of asymmetry on the flow distribution in afferent and efferent vessels and the possibility of the occurrence of a "dead point" in the posterior communicating artery were studied. The authors found that a slight asymmetric change in the right posterior communicating artery (doubling the diameter) could result in noticeable effects in the flow distribution (flow in the left carotid artery exceeded that in the right carotid artery and a small flow was present in the anterior communicating artery), but the pressure seemed to be unaffected. The authors pointed out that a dead point in the posterior communicating artery cannot occur in humans.

Hillen et al., *J. Biomechanics*, 21:807–814 (1988), simplified their model by ignoring pulsatility and vessel wall elasticity. From the comparison of the simple model and the previous model, they concluded that the deletion of pulsatility and vessel wall elasticity caused only a slight decrease of the flows without any flow redistribution. This finding was in contrast to the study of Kufahl and Clark, *J. Biomechanical Engineering*, 107:112–122 (1985), in which the flow redistribution was found to be due to pulsatile flow. The authors concluded the contradiction was caused by the ways in which the frictional resistances were determined in the different models. Hillen et al. used the Hagen-Poiseuille resistance, whereas Kufahl and Clark calculated wall friction from a quasi-two-dimensional velocity profile that is approximated by a sixth degree polynomial.

Clark et al., *Neurological Research*, 11:217–230 (1989), built four computer models for the human Circle of Willis. The first model contained 73 vessels ("model 73") representing the basic circle and served as a benchmark. The second model was constructed by adding the naturally-occurring secondary anastomoses, the total number of vessels increased to 85 ("model 85"). Adding an artificial anastomosis between the frontal artery and the middle cerebral artery in model 73 and model 85 resulted in model 75 and model 88, respectively.

In order to evaluate the ability of each of the anastomotic vessels under normal conditions, Clark et al. studied five cases. In each case, a slight increase in the diameter of the anastomoses was observed over the previous model. The results showed that the EC-IC bypass was very beneficial when natural anastomoses were absent.

In another five cases, a 90-percent stenosis was imposed in the middle cerebral artery. The same studies were performed by Clark et al. as before. They found that the anastomotic channels helped supply the ischemic areas, the larger the diameter, the better the supply. Again, the artificial anastomoses were most beneficial when the natural anastomoses were not present.

Later, Charbel et al. ["Predictive value of a computerized model of the cerebral circulation", $44^{th}$ Annual Meeting of Congress of Neurological Surgeons (Chicago, 1994); "Validation and clinical potential of a computerized model of the cerebral circulation", $1^{st}$ Annual Meeting on the Joint Section on Cerebrovascular Surgery of the AANS & CNS (1996)] introduced both quantitative, semi-quantitative, as well as direct quantitative methods of validating a patient-specific computer model by directly measuring flow in blood vessels during surgery and comparing the values with the computer model. More recently, the same group began utilizing magnetic resonance as another valuable validation tool, "Phase Contrast MR flow measurement system using volumetric flow constrained image interpolation and color coded image visualization", 47th Annual Meeting of Congress of Neurological Surgeons, (New Orleans, 1997), thus further bringing computer modeling within the reach of the clinician.

Duros et al., *Neurological Research*, 13:217–223 (1991), built a 69-vessel model to simulate the cerebral circulation with an aneurysm. The mathematical method used in the model was the same as Kufahl and Clark, *J. Biomechanical Engineering*, 107:112–122 (1985). The Duros et al. model differed from the other models in that the model not only contained cerebral arteries, but also contained 30 main supply arteries to different organs of the human body.

The aneurysm was balloon-shaped, elastically tapered with zero distal flow and was placed at the junction of the internal carotid, the anterior cerebral and the middle cerebral arteries. To simulate the condition where a rupture may happen, several parameters were adjusted: all terminal vessels' resistance values were enlarged by a factor of 10 and two 80 percent stenoses were placed in the middle cerebral artery and anterior cerebral artery to flank the aneurysm. Systemic pressure was increased to 150 mm Hg to represent hypertension. The compliance coefficient of the aneurysm was set to 1.5 to represent a stiff wall condition.

Duros et al. focused on the pressure propagation inside the aneurysm and found that the pressure did not change with the neck diameter, but the pressure peak value increased by increasing the sack diameter. In order to achieve a high pressure (310 mm Hg) indicative of hypertension which may trigger the rupture of the aneurysm, an increased number of reflecting sites in both the near and far fields, and arteriosclerotic arteries were needed.

Flow branching at arterial bifurcations is an important factor in the progression of vascular disease. This blood flow through the artery bifurcation was extensively studied both by experimental and numerical methods.

Liepsch, *Biorheology*, 21:571–586 (1984), studied the non-Newtonian fluid in a T-shaped bifurcation. Perktold et al., *Biorheology*, 26:1011–1030 (1989), studied a Y-shaped bifurcation with an aneurysm in the cerebrovascular tree. Walburn, *J. Biomechanical Engineering*, 104:66–88 (1982), studied steady flow and pulsatile flow through the aortic bifurcation, secondary flow was not observed during the pulsatile flow but was observed during the steady flow. Fukushima et al., *J. Biomechanical Engineering*, 110:161–171 (1988), found secondary flow in both steady and pulsatile flow, however, the influence of the secondary flow is smaller during the pulsatile flow than during the steady flow.

To take the importance of the secondary flow into consideration, a few three-dimensional computer models have been built. Wille, *J. Biomechanical Engineering*, 6:49–55 (1984), built a single three-dimensional model of aortic bifurcation with steady flow. Yung et al., *J. Biomechanical Engineering*, 112:189–297 (1990), studied the steady flow in the aortic bifurcation. In order to generate the mesh conveniently, Yung et al. used a non-physiological area ratio of 2.0 to produce flow geometry. Perktold & Peter, *J. Biomechanical Engineering*, 12:2–12 (1990) studied the wall shear stress in a three-dimensional model of a T-shaped bifurcation. Perktold [*J. Biomechanical Engineering*, 13:464–475 (1991); *J. Biomechanics*, 24:409–420 (1991)] analyzed non-Newtonian characteristics, wall shear stress and pulsatile flow in a three-dimensional model of carotid bifurcation. Rindt et al., built a three-dimensional model for carotid bifurcation, but they used steady flow and rigid vessel wall.

The simplest blood vessel wall model is a rigid tube. However, vessel wall elasticity has an important effect on the blood flow wave propagation. For a large artery, the vessel wall is composed of three distinct layers, an intima, a media and an adventitia. Each of these layers has a unique function. The vessel wall is not only elastic but also viscoelastic. The vessel elasticity was modeled by a relationship between blood vessel cross-sectional area and local pressure. Raines proposed a widely used model:

$$A(p,x)=A(p_0,x)+\beta ln(p/p_0) \quad (4)$$

Another quadratic form used by Porenta, Balar, and Stergiopulos is:

$$A(x)=A_0(x)[1+C_0(p-p_0)+C_0(p-p_0)^2] \quad (5)$$

where $\beta$, $C'_0$ and $C'_1$ are constants which are determined by experiment.

These models are purely elastic models. However Patel and Vaishnav verified the existence of the viscoelasticity in arterial walls through a dynamic experiment. Reuderink et al. found that neglecting the viscoelasticity of the tube wall could result in an underestimation of both phase velocity and damping. Hawley discovered that a viscoelastic wall model yielded results closer to normal physiological reality than an elastic wall model.

In most computer models, arteries were treated as straight tubes. But the structure of the Circle of Willis is three-dimensional, and arteries are bent. Curvature together with pulsatile flow greatly affect wall shear stress and cause secondary flow which may be important in understanding the progression of neurovascular disease. Although curvature was not considered in prior intracranial cerebral circulation models, blood flow in extracranial curved arteries such as the aortic arch, carotid siphon and coronary arteries were analyzed by a number of researchers. Friedman and Ehrlich [Friedman and Ehrlich, *Numerical simulation of aortic bifurcation flows: the effect of flow divider curvature, J. Biomechanics*, 17:881–889 (1984)] digitized the radiography of human aortic bifurcation to obtain the contours of the artery and performed the computation of steady two-dimensional flow in the region. The results suggested that wall slope may be an important factor affecting the variability of shear stress along the medial wall. The variation in the curvature of the proximal iliac entries may affect the susceptibility of these arteries to vascular disease. Chang and Tarbell [Chang and Tarbell, *Numerical simulation of fully developed sinusoidal and pulsatile flow in the curved tubes, J. Fluid Mech.*, 161:175–198 (1985)] simulated pulsatile flow in the aortic arch and found that the secondary flow was nearly as large as the axial flow component, the secondary flow was complex with up to seven vortices and peak axial and highest r.m.s. wall shear stress were found at the inside wall. Also, the axial-flow direction was reversed at the inside wall.

Ling and Atabek [Ling and Atabek, *A numerical study of flow in curved tubes simulating coronary arteries, J. Biomech.*, 21:927–937 (1988)] simulated flow in the coronary artery using the same method of Chang and Tarbell. They found that flow was quasi-steady under resting conditions but markedly unsteady under excited conditions. Only a single secondary flow vortex was found. Perktold et al. [Perktold et al., *Wall shear stress distribution in the human carotid siphon during pulsatile blood flow, J. Biomechanics*, 21:663–671 (1988)] used two different entrance velocity profiles to study the flow pattern in a slightly curved segment of the left main coronary artery. The different velocity profiles only resulted in significant differences in the immediate vicinity of the inlet, the difference does not persist far into the artery, and significant influence of the secondary flow on the wall shear stress distribution was found.

Perktold et al. [Perktold et al., *Wall shear stress distribution in the human carotid siphon during pulsatile blood flow, J. Biomechanics*, 21:663–671 (1988)] analyzed flow in the carotid siphon and left main coronary artery. They found that the maximum secondary flow velocities were on the order of three to four percent of the maximum axial velocity and the secondary flow has an important influence on the wall shear stress distribution.

It is commonly believed that the blood behaves as a Newtonian fluid in the large blood vessel due to the high shear rate. However, some studies indicated that there were some non-Newtonian effects in the large vessel. It was also found that non-Newtonian effects exist in the low shear area near bends and bifurcations. Xu et al. [Xu et al., *Flow studies in canine artery bifurcation using a numerical simulation method, J. Biomech. Eng.*, 114:504–511 (1992)] used the Casson model to investigate the non-Newtonian effect in artery bifurcation. They found no great differences in velocity profiles. Lou and Yang [Lou and Yang, *A computer simulation of the non-Newtonian blood flow at the aortic bifurcation, J. Biomechanics*, 26:37–49 (1993)] used a weak-form Casson model to study the non-Newtonian effect in aortic bifurcation. The results indicated that the non-Newtonian property of blood did not drastically change the flow pattern, but caused an appreciable increase in the shear stress and a slightly higher resistance to both flow separation and the phase shifts between flow layers. Dutta and Tarbell [Dutta and Tarbell, *Influence of non-Newtonian behavior of blood flow in an elastic artery model, J. Biomech. Eng.*, 118:111–119 (1996)] applied a simple power law model in an elastic artery and again found the viscoelasticity of the blood does not influence its flow behavior under physiological conditions in large arteries.

The present invention is a practical integration of several aspects of cerebrovascular and computer research. A program has been developed for computer aided neurovascular analysis and simulation that is useful for assessment and prediction of cerebral circulation changes. Such a program offers significant benefit, not only for stroke victims, but also for victims of trauma or congenital circulation disease. For instance in the case of progressive occlusion, the program offers the physician the ability to track circulation deterioration and plan for the eventual loss of the vessel by allowing the physician a practical method of evaluating potential treatment options.

The program has up to four major components: (i) a vessel extraction system from Digital Subtraction Angiography (DSA); (ii) a three-dimensional phase contrast Magnetic Resonance (MR) flow measurement system and three-dimensional pulsatility visualization; (iii) a computer simulation system for cerebral circulation; and (iv) a worldwide web-based interface and window to the world.

The process involved in the present invention creates a virtual replica of the environs of the Circle of Willis or other vascular networks within the human body and computes the blood flow in this associated network. The modeling program also allows analysis and simulation of flow and pressure within the cerebrum and/or other organs under the condition of a selected blood flow perturbation (e.g., a cerebral aneurysm, stenosis, bypass, other cerebrovascular disease, trauma, etc.). The modeling program currently uses the finite-difference numerical method. Further under its various embodiments, the process may be applied to any blood vessel leading to or coming out of the brain. Also, the same process can be applied to other vascular regions of the body.

A vessel extraction system is used for determining exact vessel diameters for use in the model. The vessel extraction system may operate under any of a number of formats. For example under one format an Attentionally-Based Interaction Model may be used (e.g., "AIM: Attentionally Based Interaction Model for the Interpretation of Vascular Angiography" by F. K. H. Quek, C. Kirbas, and F. Charbel, IEEE Transactions on information Technology in Biomedicine, Vol. 03, No. 02, June 1999). Under another format (described below), a semi-automatic process, involving the manual identification of the vessel wall, may also be used. While either format may be appropriate, it has been found that the semi-automatic process described below provides more accurate results.

The vessel extraction system provides accurate and rapid measurement of vessel diameters and length in various predetermined regions of the Circle of Willis. The data with the smallest vessel size resolution (on the order of a few hundred microns) is currently derived from x-ray angiograms [platform: SGI Workstation, IRIS 6.2/6.4 Varsity Package (Rapidapp, Open GL, Open Inventor, C++)].

The use of digital x-ray angiography and computerized acquisition of the digitized picture can accelerate and enhance the data acquisition process over manual reading of vessel diameters from the x-ray angiogram. The two-dimensional nature of current x-ray angiographic measurements limits the ability to derive detailed three-dimensional data from the technique.

Magnetic resonance imaging (MRI) has developed in such a manner that useful three-dimensional data pertaining to vessel size and flow are obtainable. The source of data is from magnetic resonance imaging which uses three-dimensional phase contrast angiographic methods to measure flow [platform: SGI Workstation, IRIS 6.2/6.4 Varsity Package (Rapidapp, Open GL, Open Inventor, C++)]. On its own, the vessel size resolution f the MRI data is on the order of a half a millimeter.

The use of these data in the three-dimensional phase contrast magnetic resonance (MR) flow measurement system of the invention enhances the accuracy of the cross-section and flow measurements by three-dimensional localization and visualization of the vessels. Microfiche Appendix A is a copy of the three-dimensional phase contrast magnetic resonance flow measurement system and three-dimensional pulsatility visualization system program.

Turning now to image processing, the vessel extraction system will be discussed. For the interactive approach to be effective, it must exploit the facility of humans to operate or communicate within the bounds of certain rules which govern the approach. As will become apparent, the vessel extraction system is a selective interaction paradigm for the analysis of multimodal medical images (e.g., magnetic resonance angiography (MRA), magnetic resonance imaging (MRI), xenon computed tomography (XeCT), x-ray angiograms (XRA), etc.).

FIG. 1 is a block diagram of a cerebral modeling system 10, generally in accordance with an illustrated embodiment of the invention. The modeling system 10 generally includes a data source, 12, a central processing unit (CPU) 14, a display 18 and a keyboard 16. The data source 12 may one or more medical imaging systems (e.g., MRA, MRI, XeCT, XRA, etc.).

In the system 10, the user selects the context from a menu (or a schematic diagram of the neurovascular system) and manipulates a cursor through the data using a 2D or 3D pointing device. For example, FIG. 2 shows the human Circle of Willis 100, including, 108 blood vessels. Selection of one of the vessels provides the system 10 with a context of what to look for.

Figure 3:
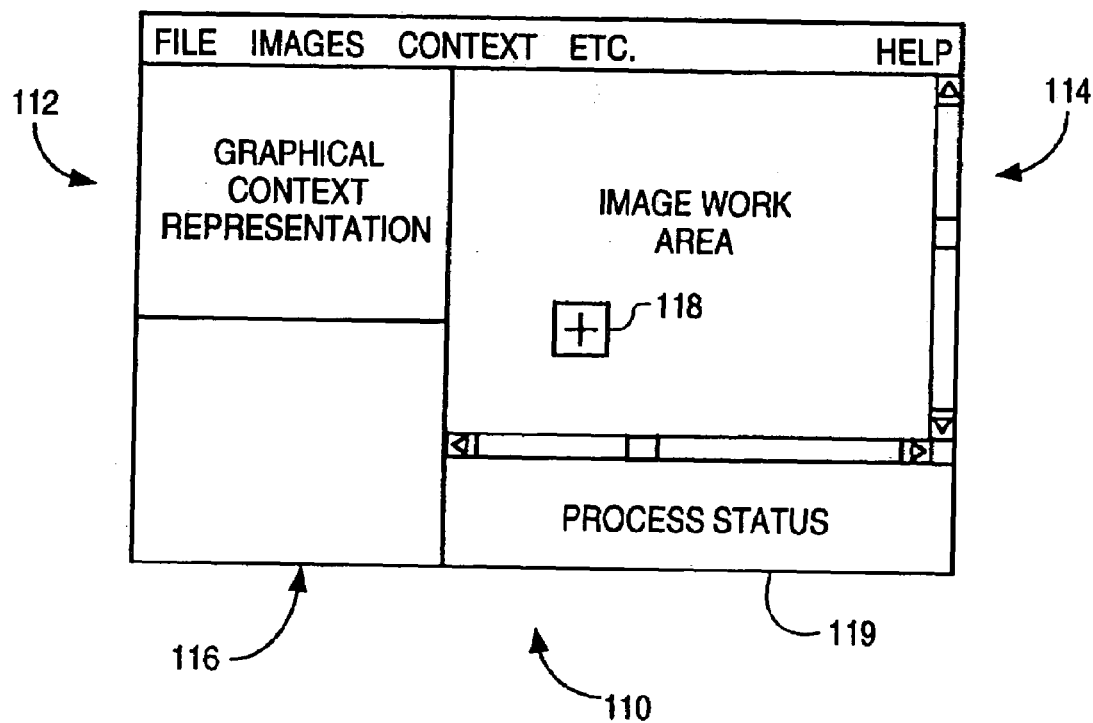
FIG. 3 is an operator interface used by the system of FIG. 1.

FIG. 3 shows an interactive screen 110 that may be presented on the display 18 of the system 10. The Circle of Willis 100 of FIG. 2 may be displayed as a graphical context representation in a box 112 of the screen 110. An operator (not shown) of the system 10 may select a vessel (e.g., 102) using the cursor 118.

Once a context has been selected in the first box 112, the operator may show the CPU 16 where to look for the vessel in the image work area 114. The operator may identify the vessel 102 by placing the cursor 118 over the vessel and activate an ENTER button (click on the mouse).

Figure 4:
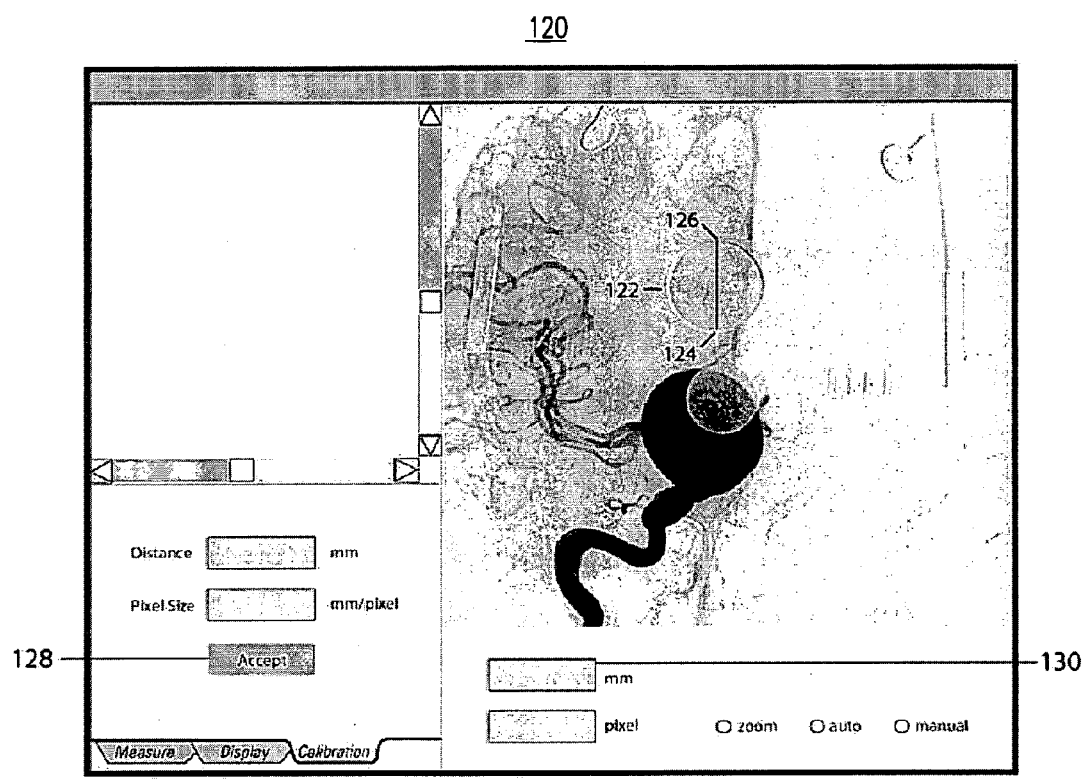
FIG. 4 is a system calibration screen used by the operator interface of FIG. 3.

However, as a first step, the user may also choose to calibrate the vessel extraction system using the screen 120 shown in FIG. 4. To calibrate the vessel extraction system, a known metal object (e.g., a penny) 122 may be placed on the cheek of a patient during data acquisition. The vessel extraction system may be calibrated by measuring the metal object 122.

To calibrate the vessel extraction system, the user may place the cursor 118 on one side of the metal object 122 and activate ENTER (click on the mouse) to identify a first side of the metal object 122. The user may then drag the cursor 118 across the metal object or simply click on the opposing side of the metal object 126.

A distance measured by the vessel extraction system may appear in a first box 130. If the measured distance is accurate, the operator activates an ACCEPT button 128. If the measured distance is not accurate, then the operator may adjust the pixel size to correct any error.

Figure 5:
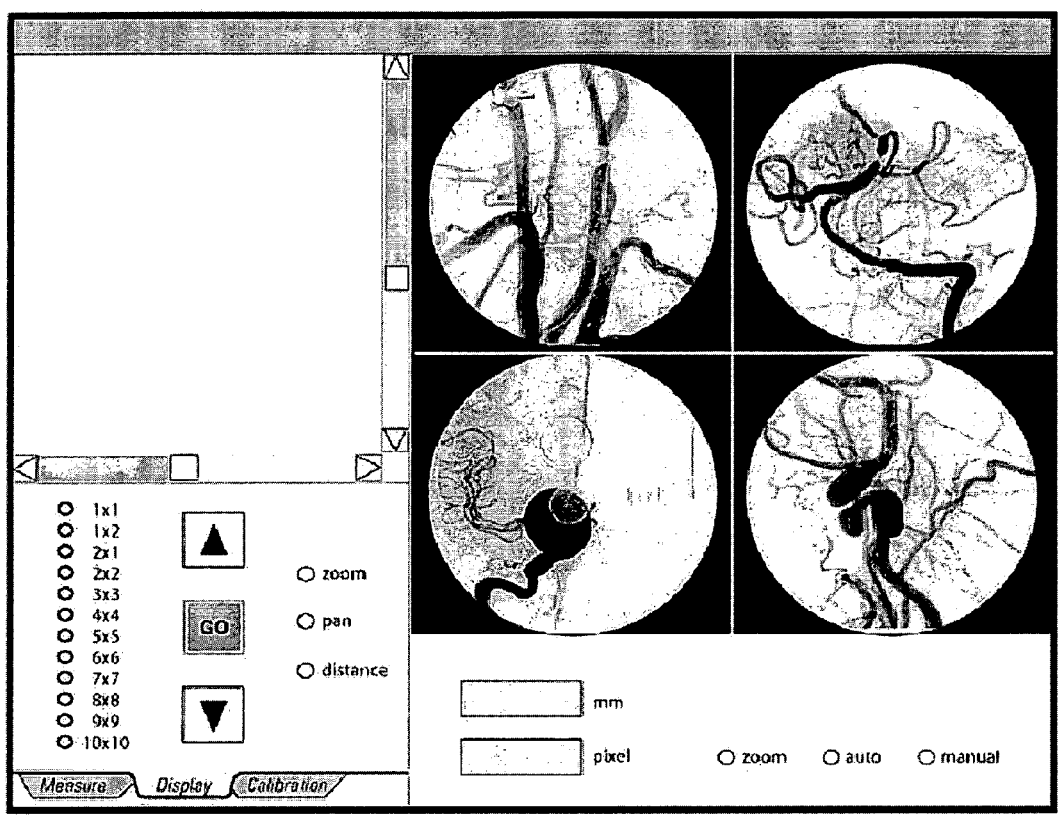
FIG. 5 is a vessel selection screen used by the system of FIG. 1.

Once the vessel extraction system has been calibrated, the operator may proceed to customize the cerebral model to the precise characteristics of the patient. As a first step, the operator may select the screen 130 shown in FIG. 5 by selecting the appropriate softkey along the lower edge of the control area 116. Shown on the right side in the image work area 114 may be any number of different cranial slices. Shown in the upper left in the graphical context box 112 is a portion of the cerebral vascular structure.

Using a set of controls in the image control area 116, the operator may view the entire vascular structure 100, or any portion. The operator may zoom-in or out by selecting the appropriate softkey.

Similarly, the operator may select any of a number of images for display in the image work area 114. Shown along the left edge of the control area 116 is a set of softkeys for selecting the number of slices to be displayed in the work area 114. The CPU 14 automatically adjusts a size of each frame to accommodate the number of frames to be displayed in the image work area 114.

To measure a vessel, the operator may select one of the frames within the image work area 114. To select an image, the operator may place the cursor 118 over an image and press ENTER. Alternatively, the operator may select the image by highlighting (i.e., clicking on) the image and selecting the softkey "MEASURE" in the left corner of the control area 116.

Figure 6:
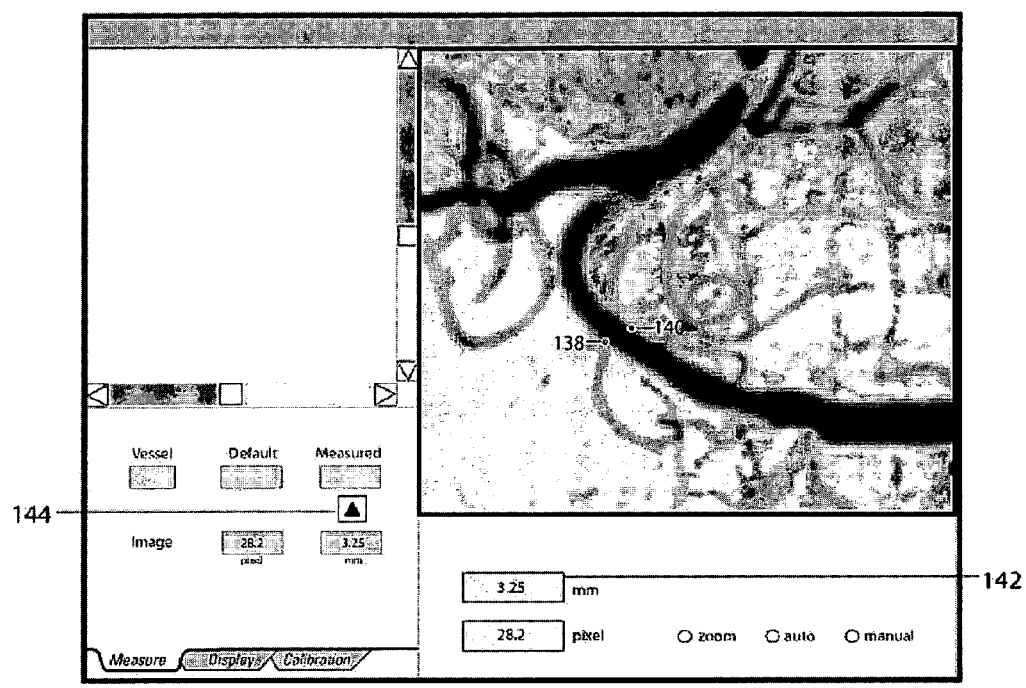
FIG. 6 is a vessel size measurement screen used by the system of FIG. 1.

Upon selecting an image, the screen 136 of FIG. 6 may appear with the selected slice within the image display area 114. Softkeys in the process status area 119 may be provided to allow the operator to zoom-in or out. By using the appropriate softkeys, the operator may position the appropriate vessel in a convenient location for measurement.

To measure a vessel, the operator may first select the vessel to be measured in the context area 112. Selecting the vessel may cause the selected vessel to appear in the color red.

Upon selecting a vessel, the operator may then identify the boundaries of the corresponding vessel in the image work area 114. To identify the vessel boundaries, the operator may first place the cursor 118 of a first edge 138 and activate the ENTER key. The operator may then place the cursor 118 or the opposing edge of the vessel and identify that edge to the CPU 14 in a similar manner.

The CPU 14 determines the distance between the two selected points 138, 140 and displays the measured value in a display box 142. The operator may enter the value by selecting an accept box 144. Once entered, the measured dimension may be stored along with an identifier of the measured vessel.

Once the operator has measured a corresponding vessel, he/she may return to the first screen 130 and select another frame and measure another vessel. The process of selecting frames and measuring vessels may continue until some or all of the vessels have been measured.

Once the corresponding vessel has been identified and measured, a blood flow may be measured in that vessel. Blood flow may be determined using the three-dimensional location and orthogonal slice crossing that vessel.

The actual determination of blood flows is part of a multi-step process referred to as cine phase contrast magnetic resonance (PCMR). Two-dimensional localization using cine PCMR requires positioning a line perpendicular to a centerline of a vessel of interest on a magnetic resonance angiography (MRA) image. Since it is often difficult to position a line perpendicular to the centerline, a three-dimensional process was developed.

The 3-D localization method of slice selection was developed using a 1.5 T imager (manufactured by GE of Milwaukee, Wis.). An axial MRA with zero interspacing covering the circle of Willis was gathered and transferred to a SGI workstation. A stack of 2D images can then be converted into 3-D volume data. The volume data can be described as follows:

$$V(x,y,z) = I_k(x,y),$$

where $k=0, 1, \ldots N-1$, $z=k*T$, $I_k(x,y)$ is the kth MRA image, T is the slice thickness, and N is the number of slices. The x-axis is from right to left, y-axis is from anterior to posterior and z-axis is from inferior to superior.

Given a volume of voxels $V(x,y,z)$, an iso-surface in the form of a polygonal mesh can be generated using a Marching-Cube algorithm. For a given iso-surface value, each voxel can be classified into one of two types: one where the value at the voxel is greater than or equal to the iso-surface value. The other where the value is smaller than the iso-surface.

According to the voxel type, a cube consisting of eight adjacent voxels may have 14 different configurations. The points of intersection between surface and the edges of the cubes can be generated by linear interpolation between values at the vertices. The triangular polygons may be used to tessellate these intersections.

The iso-surface may be determined from a maximum intensity projection (MIP) using an appropriate 1.5 T imager (e.g., GE) as a data source 12. The procedure for determining such an iso-surface is as follows.

The region encompassing the vessels of interest and the iso-surface value were obtained. The window level and the window width for changing the contrast of the MIP image were adjusted so that the vessels of interest were enhanced and the background was suppressed. The iso-surface value was determined as follows:

iso-surface value=window level−(window width/2)

Next, the iso-surface of cerebral vessels can be rendered by converting these triangular polygons into a scenegraph object using an appropriate software tool (e.g., "The Inventor Mentor: Programming Object-Oriented 3D Graphics with Open Inventor, Release 2", Josie Wernecke, Addison-Wesley Publishing Co., 1994). The vessel of interest can easily be found through user interaction with the 3D scenegraph by rotating, translating, and zooming in and out on the 3D object. According to the orientation of the vessel, an image plane (either axial or sagittal or coronal cut) can be selected by the operator for localizing the vessel of interest. The plane 146 may be chosen such that it is visually closest to the plane that is perpendicular to the flow direction of the vessel (e.g., a sagittal cut for the middle cerebral artery shown in FIG. 9a).

Figure 9A:
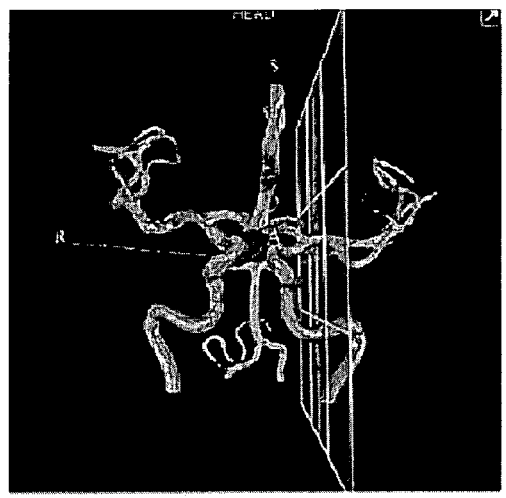
FIG. 9 depicts a sagittal plane and vasculature obtained using the Marching-Cube Algorithm by the system of FIG. 1.
Figure 9B:
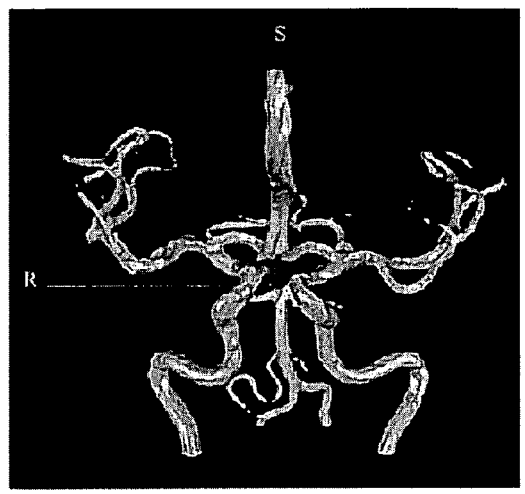

FIG. 9a shows a sagittal plane for determining slice orientation for a middle cerebral artery. FIG. 9b shows the 3D vasculature obtained using the Marching-Cube Algorithm.

Once the plane is selected, the 2D image associated with the plane can be calculated based upon the original volume of voxels and the vessel measured as described above. For an axial cut, the 2D image is the same as the original image. For a sagittal cut, the 2D image can be obtained through the expression:

$$I(y,z) = V(X,y,z),$$

where X is the coordinate of axis x for the sagittal plane. For a coronal cut, the 2D image can be obtained through the expression:

$$I(x,z) = V(x,Y,z),$$

where Y is the coordinate of axis y for the coronal plane.

The cross-section of the vessel of interest in the 2D image can then be specified by drawing a region of interest (ROI) in the 2D image and the ROI can then be drawn in the 3D vasculature. The localization of the vessel of interest can then be achieved by correlating the ROI in the 2D image and the ROI in the 3D image.

To obtain the border of the vessel in the 2D image, the ROI is refined by image segmentation using thresholding. The center of the refined ROI may then be calculated. By moving the plane along the vessel segment, a set of center points of the vessel may be identified. A line-fitting algorithm may then be used to fit these points to one line or more than one line. In the case of more than one line, the one with the maximum length and which line length exceeds a specified slice thickness may be chosen. The center of the line and an end point of the line may be saved and provided as an input to the imager 14 as the start and end location of the cine PCMR protocol in no particular localization mode.

Figure 7A:
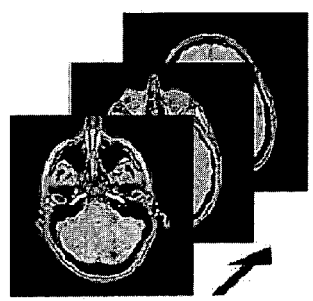
FIG. 7 depicts a series of images generated by the system of FIG. 1.
Figure 7B:
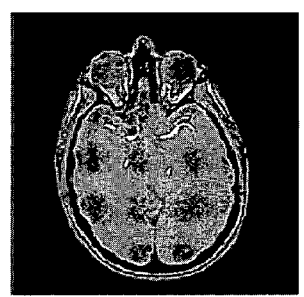
Figure 7C:
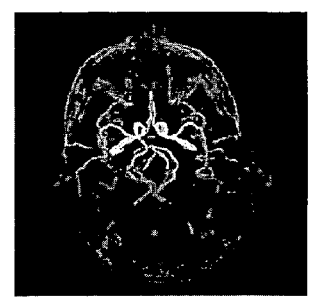
Figure 8:
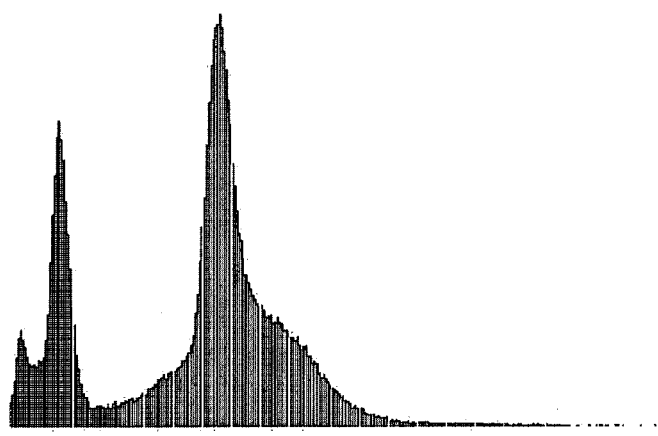
FIG. 8 depicts a histogram of an MIP image for determining an iso-surface by the system of FIG. 1.

There may be many vessels including arteries and veins in a cine PCMR image. To identify those vessels in a cine PCMR image often becomes difficult when the slice orientation is obtained using an oblique cut. Identification of the vessel has been found to be much simpler if the slice orientation is obtained using the 3D localization described above. The vessel of interest is usually proximate the center of the cine PCMR images when the 3D localization is used. The slice orientation can be drawn into the 3D vasculature when needed so the operator can see where the slice orientation and vessel of interest is actually located in the 3D vasculature. FIG. 9b shows the 3D vasculature obtained using the images shown in FIG. 7a.

Figure 10:
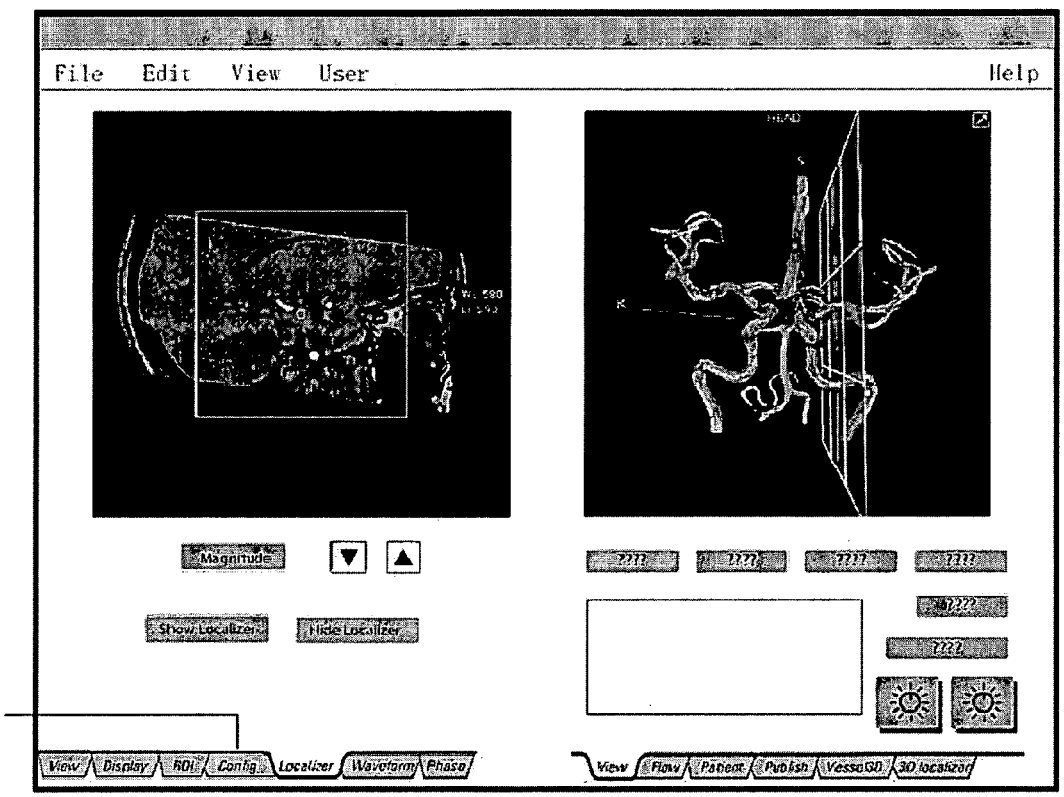
FIG. 10 depicts a screen used in flow measurement by the system of FIG. 1.

The binary masks corresponding to the ROIs drawn at each time point in the cardiac cycle for vessel diameter measurement may then be passed to the flow calculation program. FIG. 10 shows a screen 150 that may be presented to the operator. Shown in the image work area 114 of the screen 150 is a plane passing through a vessel of interest. Shown in the graphical context area is a ROI 148, surrounding the vessel of interest.

Figure 11:
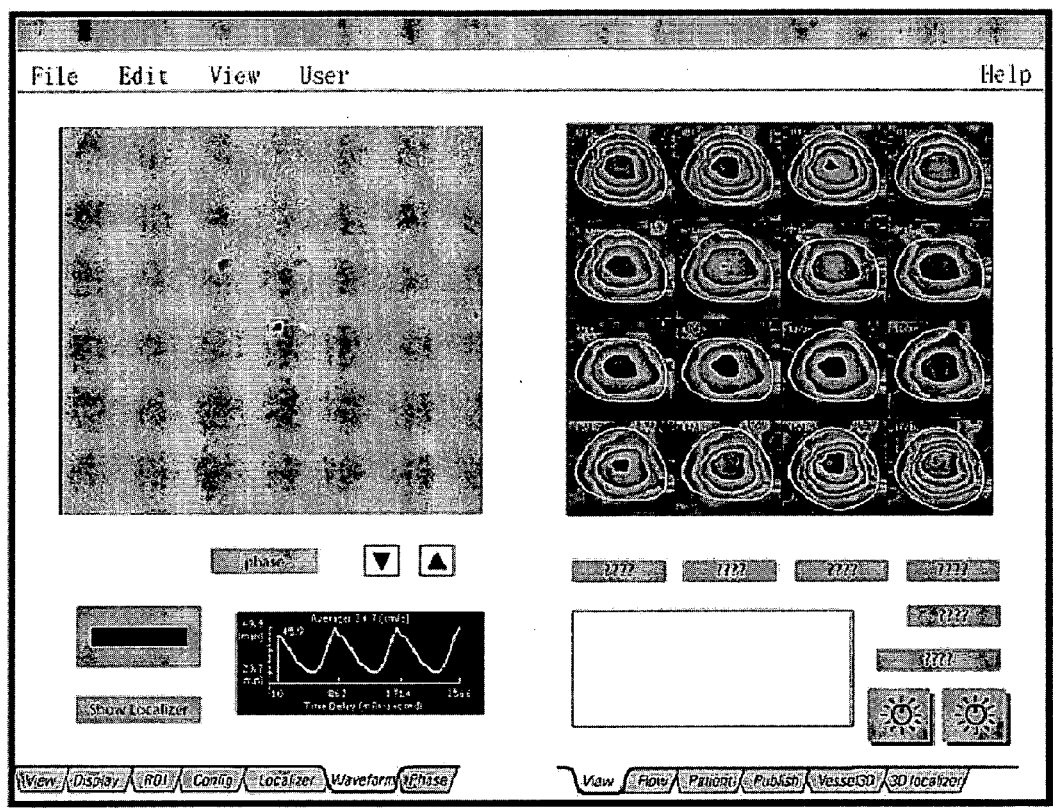
FIG. 11 depicts color-coded flow of a region of interest used by the system of FIG. 1.

The operator may select a waveform softkey 152 to view bloodflow. In response, the screen 154 of FIG. 11 may be presented to the operator. The FOI 148 continues to be displayed in the context area 112. However, in the image work area 114, a phase-contrast image of blood flow is now presented.

Using the phase-contrast image, blood flow may be calculated based upon phase-shift information. The flow in a pixel may be calculated by multiplying the velocity of that pixel by the pixel area. The flow through the vessel may be determined by adding together the flows from all the pixels in the measured vessel. The cine PCMR may also record the ROI area, minimum, maximum and mean velocities in each ROI at each time point of the cardiac cycle.

Figure 12:
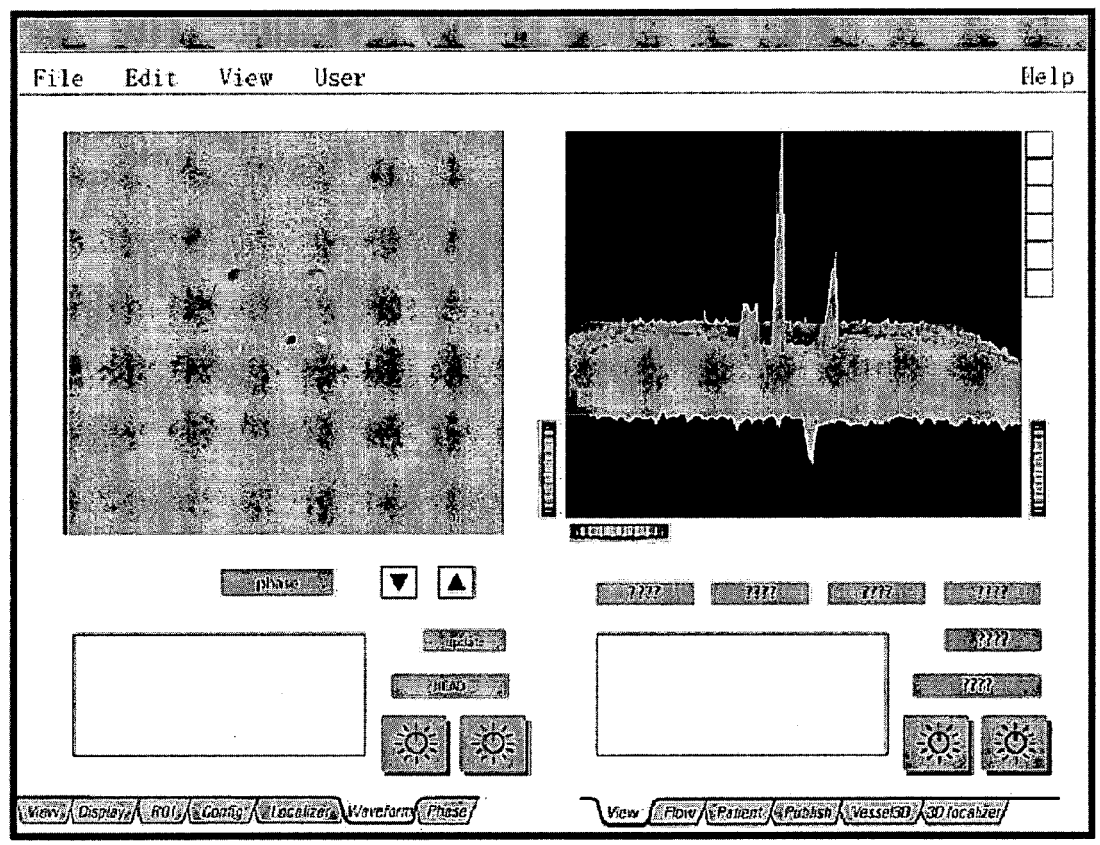
FIG. 12 depicts a graphical representation of blood flow used by the system of FIG. 1.
Figure 13:
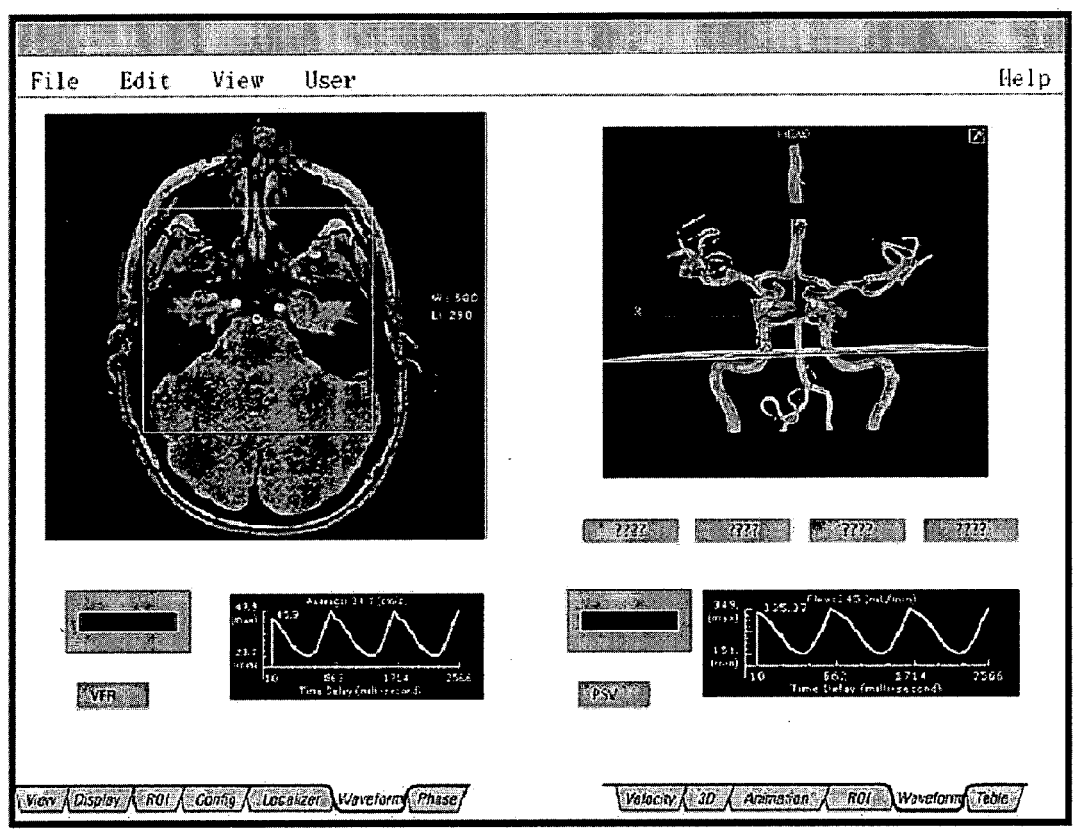
FIG. 13 depicts a vasculature structure and slice image used by the system of FIG. 1.

The flow waveforms and maximum velocity waveforms can then be plotted over the time course of the heartbeat as shown in the work area 114 of screen 156 of FIG. 12. The vasculature and source of the bloodflow may also be retrieved by the operator as shown in the context area 112 of screen 158 of FIG. 13.

Mean flow value provides a single quantity called volumetric flow rate (VFR). The mean flow is calculated by summing up all the mean flow values (all of the VFRs) throughout the cardiac cycle and then dividing by the number of cardiac frames using the expression:

$$VFR = \frac{\sum_n VFR_n}{N},$$

where VFR is the mean volumetric flow rate, n is the cardiac frame index and N is the total number of cardiac frames.

As described above, vessel size and location may be obtained from MRA, MRI, XeCT or XRA data. The dimensional information derived from the data may be enhanced using MRI operating in the phase contrast mode. The use of phase contrast MRI allows volumetric blood flow to be determined by measuring blood velocity across a cross-section of each vessel.

The enhancement of the accuracy and vessel size resolution arises from the three-dimensional reconstruction of the vessels that currently uses an interpolation scheme that is constrained by a piecewise smooth volumetric flow equation. The flow data are corroborated by transcranial Doppler measurements at predetermined vessel intervals. The flow velocity has also been found to vary as a result of vasoreactivity. Benchmark values for cerebral autoregulation have been established and are continuously refined.

The data analysis system supports both automatic and interactive extraction of the vessel cross-sections. A color coding scheme facilitates visualization and user interaction with the data to reduce the inter-user variability.

For example, a user can view, move and freely rotate a three-dimensional picture of the cerebrovascular network 100. The user can also place a plane anywhere in the three-dimensional picture, then view the two-dimensional cross-section of the cerebrovascular network 100 at that location.

The vessels are clearly discernible in the cross-section, with color coding to denote flow into and out of the planar cross-section. The pulsatility of blood flow can be animated and visualized in the currently-developed user interface 150 in three dimensions. A vessel can be selected by the user for detailed and graphical analysis of the flow through the vessel cross-section that shows the pulsatile flow changes animated in time.

The computer simulation system 10 for cerebral circulation employs the outputs from both the vessel extraction system and the three-dimensional phase contrast MR flow measurement system to calibrate, customize and drive the cerebral circulation model [platform: PC (Pentium), Windows95/NT or DOS, Lahey Fortran 77]. The model is reconfigurable to account for person-to-person variability in the cerebrovascular network. The overall number of vascular segments in the flow model can be increased or decreased as needed to form a customized model for each patient.

The computer simulation system is flexible and accommodates empirical observations of measurements from the x-ray and magnetic resonance angiograms as well as from direct measurements of flow using flowmeters during surgery, and transcranial Doppler (TCD) at selected sites.

Figure 29:
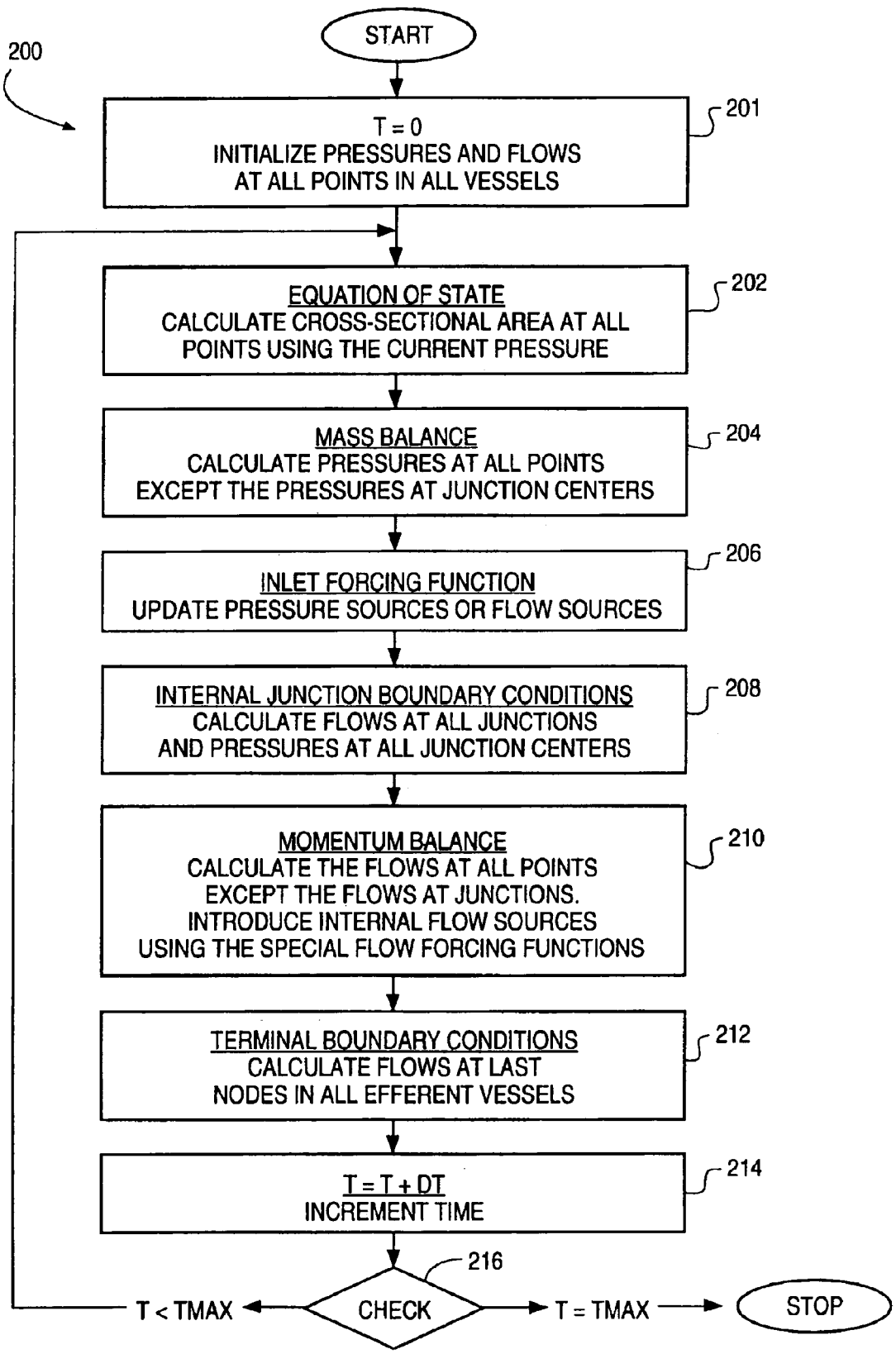
FIG. 29 is a flow chart for sequencing calculations for the model used by the system of FIG. 1.

The computer model is a one-dimensional, explicit, finite-difference algorithm based on a conservation of mass equation, a Navier-Stokes momentum equation, and an equation of state releating local pressure to local size of artery applied at each vessel segment [Kufahl & Clark, *ASME J of Biomech. Eng.* 107:112–122 (1985)]. Microfiche Appendix B is a copy of the current computer model program. FIG. 29 is a flow chart of the modeling program.

Since the arterial networks contain vessel loops (as well as many branchings), the pressure and flow nodes are staggered throughout the model. Each vessel is divided into many segments; the flow nodes are located at segment ends, the pressure nodes at segment centers. Any multi-vessel network configuration can be specified solely from the data file. Microfiche Appendix C is a sample data file with the computer parameters for a typical human model.

The model is forced by one or more pressure or flow signatures at appropriate locations. Usually, a pressure-time signature at the root of the aorta, obtained from prototype measurements serves as the forcing function.

As shown (FIG. 29), the model of the system 10 is first initialized 202 with initial pressures and flows at all nodes in all vessels. A cross-sectional area is calculated 202 for all points using the current pressure. The mass balance is determined 204 by calculating pressures at all points except the pressures at vessel junction centers. An inlet forcing function is invoked 206 to update pressure and flow sources. The internal junction boundary conditions may be evaluated 208 by calculating flows at all junctions and the pressures at all junction centers.

A momentum balance may then be determined 210 by calculating the flows at all points except the flows at junctions. A set of terminal boundary conditions may be determined 212 by calculating the flows at the last nodes in all efferent vessels.

Finally, the current time value is incremented 214 and the incremented time is compared 216 with a modeling period. If the incremented time is less than the modeling period, the process 200 repeats. If not, the process terminates.

A baseline vessel network 100 is used in the current model, including the Circle of Willis, ophthalmic arteries and other natural anastomoses. When surgical anastomoses are considered, the number of vessels can rise as needed. In addition, segments stenosed (perturbed) by any specified amount can be placed in any number of vessels. Aneurysms can also be simulated at various sites in the network. The results of any of a number of surgical procedures may be accurately predicted based upon the model results of the system 10.

A worldwide web-based interface and window to the world is available to provide blood flows and simulation results to physicians and surgeons of remotely located patients.

Early models of blood flow in the brain were based upon an assumption that any particular artery feeds a particular part of the brain. The volume of brain fed can be calculated. First, the total mass of the brain can be determined. Then, the portion fed by a particular artery can be determined as a percentage of the determined total. Knowing the mass of brain fed by a particular artery allows the volume of blood necessary to feed that mass to be determined. Those early models were general, using nominal values for the elasticity of the blood vessels, the viscosity of the blood, and the vasculature arrangement of a normal patient's brain circulatory system.

The present invention is a refined model that is capable of being adapted to specific patients. Once the volume flow of blood in certain arteries of a given patient has been determined, the model's terminal resistance pattern is determined for that patient.

Deviations of the arterial structure of the blood supply of the patient's brain from the general model are identified from the angiograms. An x-ray angiogram (XR angiogram) of the patient's brain is used to determine the diameter of the blood vessels. Phase contrast Magnetic Resonance imaging angiography (MR angiography) is then used to determine an actual blood flow in critical arteries in the brain. Missing or additional arterial segments may be identified and used to adjust the model. A knowledge of the actual arterial structure and actual blood flows can be used to customize the model to the actual patient.

To validate the 3D localization of slice selection for cine PCMR imaging, a flow phantom was constructed shown in FIG. 14a. The cylinder is about the size of a human's head and filled with distilled water. Inside the cylinder there is a cube-like frame consisting of nine Plexiglas tubes of two different diameters. Those tubes are connected with each other sequentially. The tubes were circular in cross-section with inner diameters of ¼ and ⅜ inches, i.e., 6.35 mm and 4.76 mm. The fluid used in the experiment was 5 liters distilled water doped with gadolinium chloride-EDTA.

To validate our flow measurement, both constant flow and pulsatile flow were evaluated. Axial 3D time of flight (TOF) images were acquired for the 3D localization. The images were extracted and transferred to a SGI workstation during scanning. The 3D cube-like frame was then reconstructed using the marching cube algorithm described above. The coordinates required for an oblique cine PCMR were determined using the 3D localization. Cine PCMR images perpendicular to the tubes were acquired with those coordinates. A person's heart rate was used to trigger the sequence. All the images were extracted and transferred to a SGI OCTANE workstation for flow calculation. All the flows were evaluated using the software system CMIS implemented in C++, X/Motif, and Open Inventor on the SGI OCTANE workstation.

To maintain a constant flow, the drained-out water was frequently poured back into the supply container. The flow rates were measured by timing the filling of a graduated cylinder as the actual flow rates. The slice selections of the eight tubes were determined using the 3D localization and validated with the spatial relationships of the tubes in the phantom. The cine PCMR were performed based on these slice selections. The PCMR flow rates were evaluated using the CMIS system and compared with the actual flow rate. Three different flow rates were achieved by adjusting the height of the supply container. The PCMR flow measurements were evaluated and also compared with the actual flow rates in the three different actual flow rates.

Pulsatile flow was obtained using a valve system. An inline transonic flow probe was used for measuring the pulsatile flow rates for comparison. The PCMR flow measurements were evaluated and also compared with the manually-obtained flow measurements A misalignment of 10°, 20°, and 30° for the central tube were calculated. The flows under the three different misalignments and the flow under no misalignment were evaluated and compared with the flow readings from the flow probe. The accuracy of the flow measurement under the three misalignments were obtained and compared with that under no misalignment.

Two healthy volunteers were evaluated with cine PCMRA images using the 3D localization. A volunteer carotid study was performed to study the effect of the misalignment on the in vivo flow measurements. Three misalignments of 10°, 20°, and 30° for the left common carotid artery were calculated. The flows under three misalignments were compared with the flow measured under no misalignment. The second volunteer study was performed to validate the accuracy of the slice selections for major arteries in the cerebral circulation determined by the proposed 3D localization. The slice selections for the major arteries in the cerebral circulation were calculated using the 3D localization. Cine PCMR were performed based on these slice orientations and the flows were evaluated. A peripheral gating was used to trigger the cine PCMR sequence. The following parameters were used in the cerebral blood flow protocol: TR, 33 ms; TE, minimum; flip angle, 30; number of excitations, 2; field of view, 16 cm; image matrix, 256×128; number of phases, 32; slice thickness, 5 mm for carotids, velocity encoding (VENC), 100 cm/sec for carotid, vertebral, and basilar artery, 70 cm/sec for other vessels.

Figure 14B:
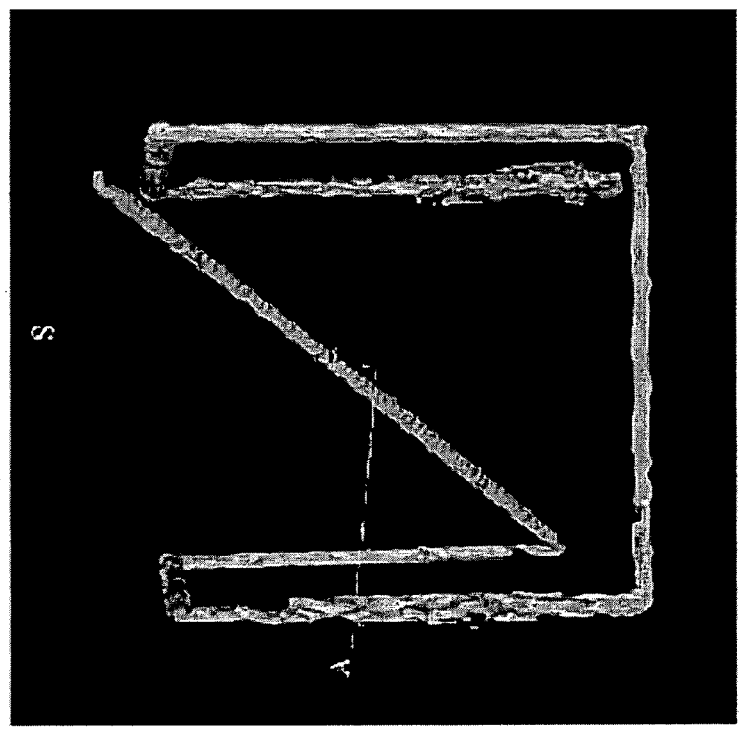
FIG. 14 depicts a flow phantom and surface rendering of the flow phantom used by the system of FIG. 1.
Figure 14:
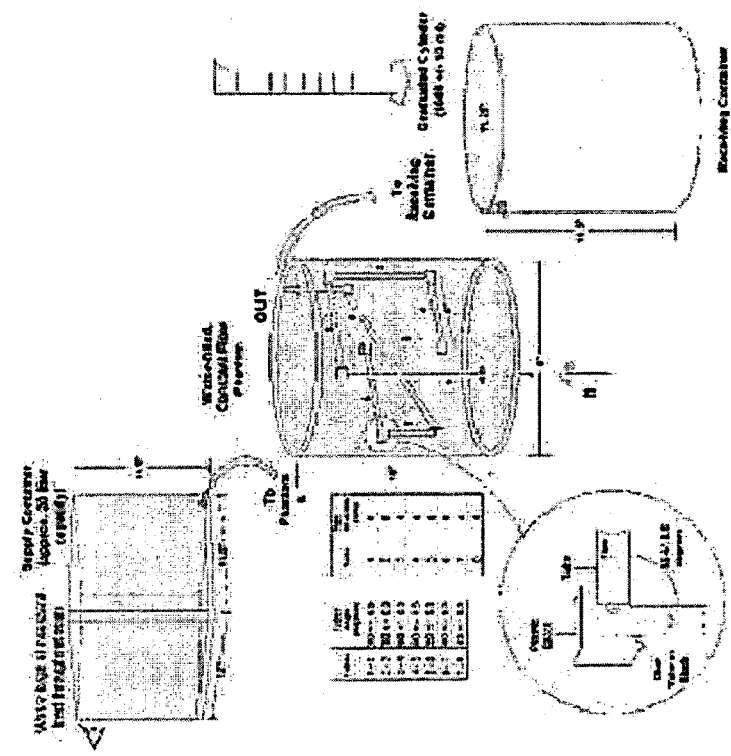
Figure 15:
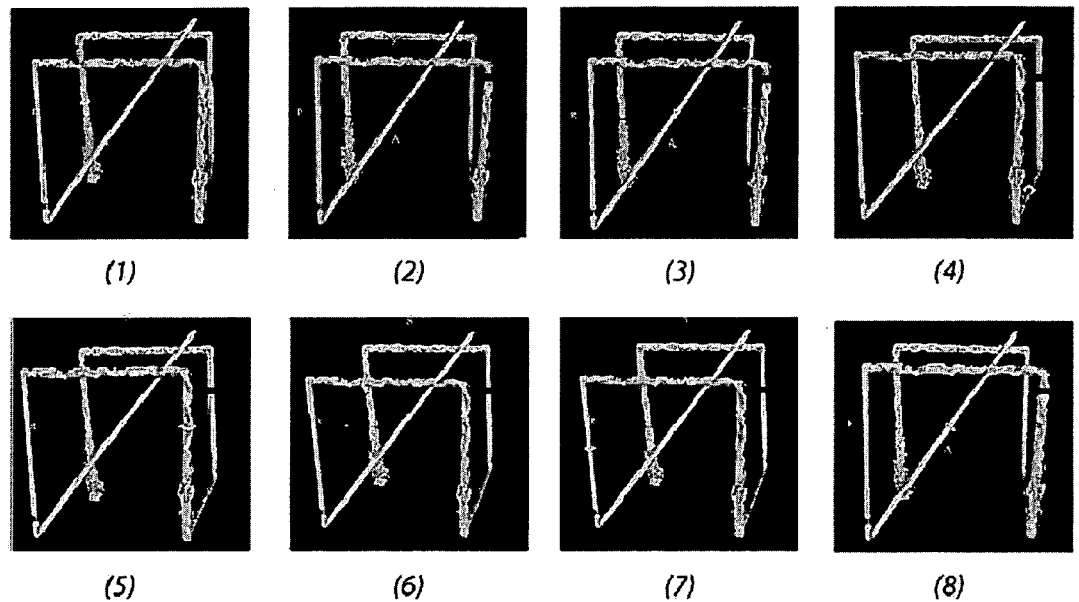
FIG. 15 depicts slice sections of the flow phantom of FIG. 14.
Figure 16:
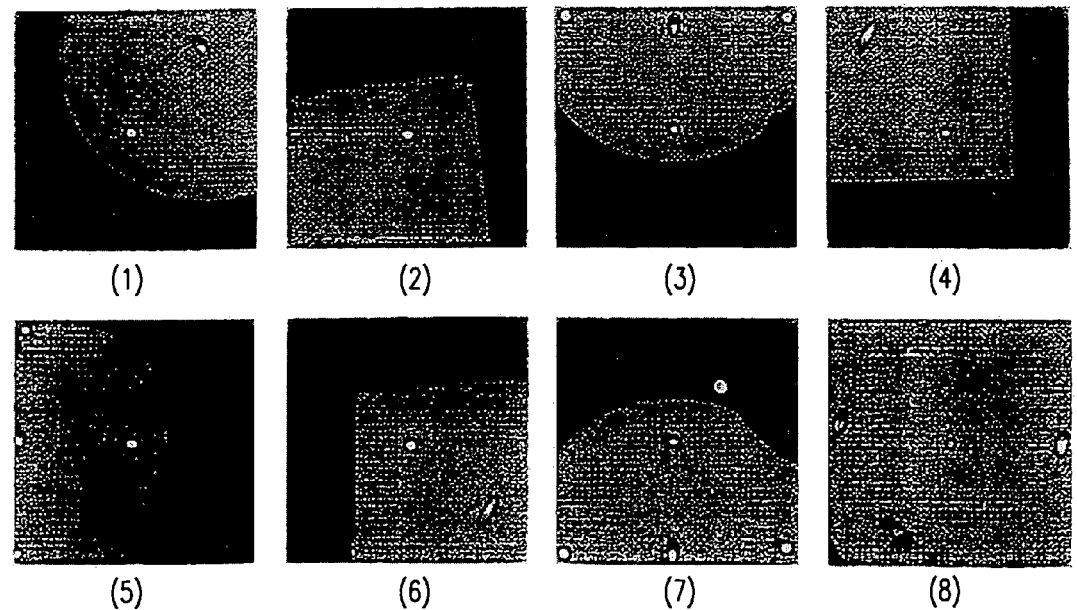
FIG. 16 depicts Cine PCMR magnitude images used by the system of FIG. 1.

The 3D surface rendering of the phantom is shown in FIG. 14b. There are three lines in the center of the bounding box. The respective lines in FIG. 14b represent Right, Anterior and Superior directions respectively. The slice selections for eight tubes are shown in FIG. 15. The tubes were labeled from 1 to 8 according to the slice selections shown in FIG. 15. Since the landmark of the head coil was set to the center of the cylinder, tube 1 is in the right and posterior position, tube 2 is in the superior and posterior position, and so on. The cine PCMR magnitude images for the eight tubes are shown in FIG. 16. The tubes of interest in FIG. 16 are all about in the centers of these cine PCMR images, circular and bright. The black rings shown in FIG. 16 are the tube walls. The large black areas and large gray areas shown in FIG. 16 are outside the cylinder (i.e., air) and inside the cylinder (i.e., water), respectively.

The coordinates of the central points for all the eight slice selections were obtained from the 3D localization and given in Table 1. These coordinates are all consistent with the positions of tubes. Table 2 gives the flow measurements calculated using the two methods described below from CMIS system and the accuracy of the flow measurements. The actual flow rates for all the tubes are the same since they are sequentially connected with each other. The actual flow rate is 330 ml/min. The difference between Method 1 and Method 2 is that Method 2 uses the flow offsets estimated from a cine PCMR imaging with no flow in the tubes while Method 1 does not use any flow offsets. The flow offsets of 16 ml/min and 8 ml/min for the tubes with diameters of 6.35 mm and 4.76 mm were calculated from the cine PCMR acquired using the same coordinates as tube 1 and tube 8, respectively, but with no flow in the tube.

TABLE I show coordinates of the center points of the eight slice orientations. (R, A, and S stand for Right, Anterior, and Superior, respectively. The unit of the coordinates is mm.)

TABLE I

|   | 1 | 2 | 3 | 4 | 5 | 6 | 7 | 8 |
|---|---|---|---|---|---|---|---|---|
| R | 51.5 | 8.1 | −49.7 | −51.4 | −52.7 | 8.8 | 47.5 | 4.5 |
| A | −49.5 | −45.2 | −51.7 | 0.0 | 51.5 | 58.5 | 54.0 | 4.0 |
| S | −5.3 | 48.7 | 2.7 | −62.2 | −7.3 | 34.7 | −5.3 | −7.3 |

TABLE II shows constant flow for eight tubes. (The actual flows for all the eight tubes are 330 Ml/min. Method 1 does not use any flow offsets while Method 2 uses flow offsets. The flow offsets for the tubes with diameters of 6.35 mm and 4.76 mm are 16 Ml/min and 8 Ml/min, respectively. The units for flow are Ml/min.)

TABLE II

|   | 1 | 2 | 3 | 4 | 5 | 6 | 7 | 8 |
|---|---|---|---|---|---|---|---|---|
| Method 1 | 347.21 | 320.03 | 319.13 | 337.89 | 343.77 | 347.39 | 318.82 | 341.82 |
| Accuracy | 5.2% | −3.0% | −3.3% | 2.4% | 4.2% | 5.3% | −3.4% | 3.6% |
| Method 2 | 331.21 | 336.03 | 327.13 | 329.89 | 327.77 | 331.39 | 326.82 | 333.82 |
| Accuracy | 0.4% | 1.8% | −0.9% | 0.0% | −0.7% | 0.4% | −1.0% | 1.2% |

TABLE III shows diameter measurements for eight tubes. (The unit for the diameter is mm)

TABLE III

|   | 1 | 2 | 3 | 4 | 5 | 6 | 7 | 8 |
|---|---|---|---|---|---|---|---|---|
| Actual | 6.35 | 6.35 | 4.67 | 4.67 | 6.35 | 6.35 | 4.67 | 4.67 |
| Measured | 6.24 | 6.24 | 4.6 | 4.78 | 6.36 | 6.47 | 4.6 | 4.56 |
| Accuracy | −1.7% | −1.7% | −1.5% | 2.3% | 0.2% | 1.9% | −1.5% | −2.3% |

Figure 17:
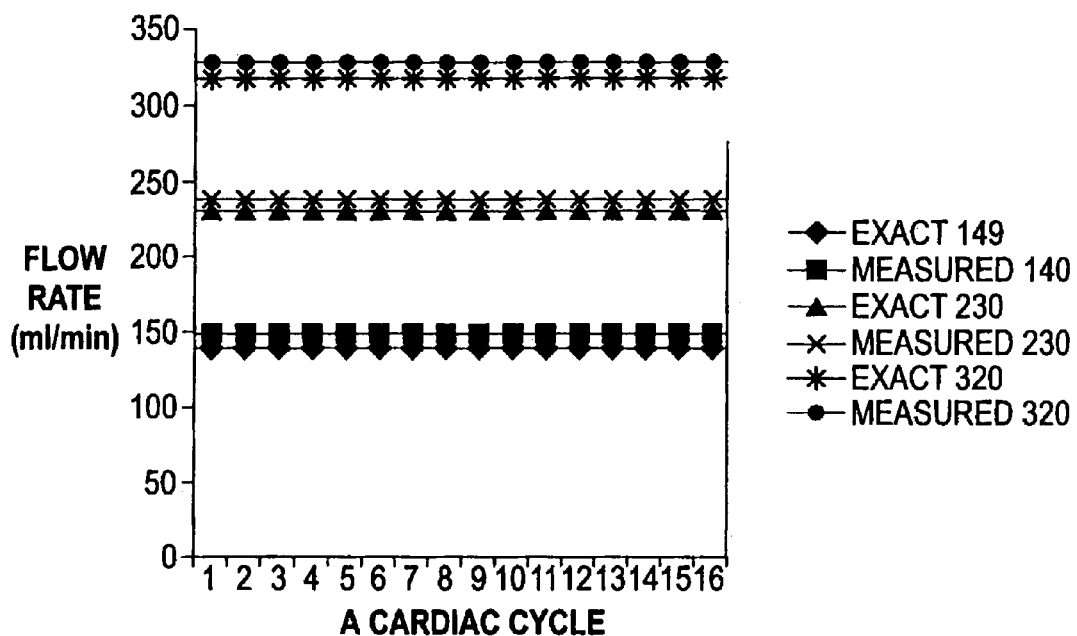
FIG. 17 depicts a comparison of flow measurements used by the system of FIG. 1.

FIG. 17 shows the comparison between the flow measurements for the tube located in the center of the phantom with diameters of 4.76 mm from cine PCMR and the actual flow rates in three different levels, i.e., 140, 230, and 320 ml/min respectively. The average flow rates estimated from cine PCMR were 150.63 ml/min, 237.70 ml/min, and 331.44 ml/min, respectively.

Figure 18:
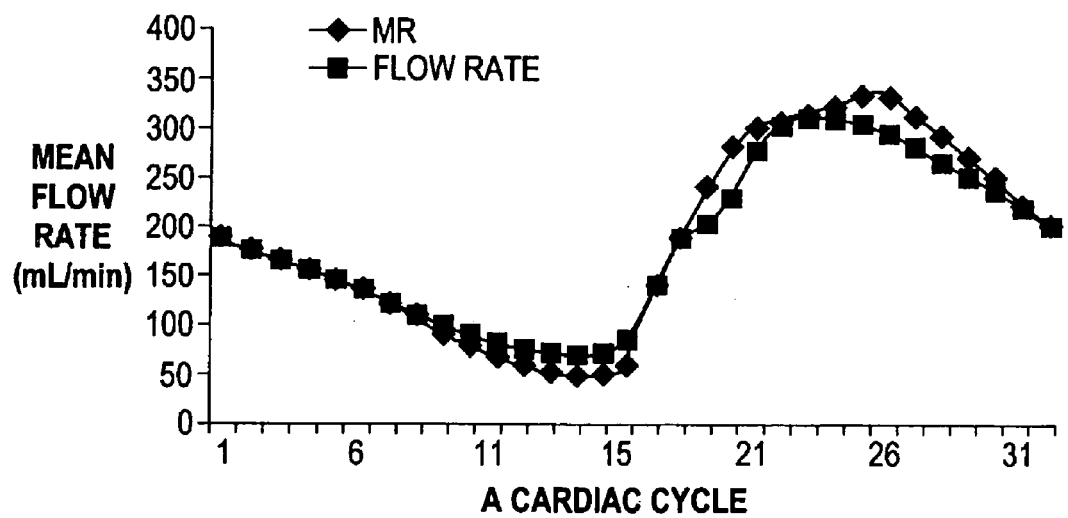
FIG. 18 depicts a comparison of flow measurements for a pulsatile flow phantom used by the system of FIG. 1.

FIG. 18 shows the comparison of pulsatile flow measurements for the tube located in the center of the phantom between PCMR and transonic flow probe. The average flow rates from both PCMR and the flow probe were 189 ml/min and 184 ml/min, respectively.

TABLE IV shows the effect of slice orientation on pulsatile flow measurements for the center tube. (Actual means the average flow rate or mean VFR obtained from transonic flow probe, MR means the mean VR obtained from PCMR measurement. The units are ml/min.)

TABLE IV

| Orientation | Actual | MR | Accuracy |
|---|---|---|---|
| 0 | 277 | 284 | 2.5% |
| 10 | 282 | 317 | 12% |
| 20 | 279 | 341 | 23% |
| 30 | 283 | 358 | 26.5% |

FIG. 19 shows the 3D surface rendering of the first volunteer's carotid under different misalignments.

TABLE V shows the effect of the misalignment on the flow measurements on the volunteer's left common carotid artery. (The units are ml/min.)

TABLE V

| Orientation | 0 | 10 | 20 | 30 |
|---|---|---|---|---|
| VFR | 545 | 544 | 514 | 488 |
| Percentage | 0% | 0% | −6% | −10% |

TABLE VI shows the flow rates of major arteries in the cerebral circulation measured in the second volunteer study. (The units are ml/min.)

TABLE VI

| LCCA | LICA | LVA | LM1 | LM2 | Lpcom | LA2 | LPCA |
|------|------|-----|-----|-----|-------|-----|------|
| 379  | 226  | 164 | 176 | 119 | 21    | 86  | 81   |
| RCCA | RICA | RVA | RM1 | RM2 | RA1   | RA2 | RPCA |
| 516  | 381  | 86  | 197 | 67  | 196   | 94  | 88   |

FIG. 20 shows some examples of the 3D localization obtained from the second volunteer study. The planes shown in FIGS. 12a, 12b, 12c and 12d give the slice selections for a left middle cerebral artery, a right anterior cerebral artery, a left posterior communicating artery, and a middle cerebral artery M3 branch, respectively.

The eight planes shown in FIG. 15 represent the eight slice selections for the eight different tubes in the phantom. The center points of the intersections between the planes and the tubes are listed in TABLE I. The position of the first point (51.5, −49, −5.3) is at right and posterior area of the phantom. This verifies that the slice selection of the 3D localization is consistent with the location of the first tube. It can also be shown that the other seven slice selections are consistent with the positions of the seven tubes. In TABLE II, the flow measurements using Method 1 have less than ±5.3% error. Using Method 2, the accuracy is less than ±1.8% error. The diameter measurements were also given in TABLE III. The accuracy for the diameter measurements is less than ±2.3% error.

To see the accuracy of flow measurement on the constant flow phantom under different flow rates, three different flow rates (140, 230, and 330 ml/min) were used. The flow measurements have an accuracy of less than ±8.0% error without flow offset compensation. If the flow offset of 8 ml/min was considered, the flow measurements have an accuracy of less than ±2.0% error.

In the pulsatile phantom study, the accuracy of the flow measurement in FIG. 18 has an accuracy of 2.7% error. The pulsatile flow waveform from PCMR is in excellent agreement with the flow waveform from the transonic flow probe. The effect of misalignment on the flow measurement of the pulsatile flow phantom can be seen in TABLE IV. The inaccuracy of the flow measurement is increased from 2.5% to 26.5% as the misalignment is increased from 0° to 30°. The misalignment effect in vivo is shown in TABLE V. Since there is no actual flow rate, the percentage changes of the flow measurements under misalignments with respect to the flow measurement under no misalignment were calculated. The percentage change of the flow measurement is increased from 0% to 10.0% as the misalignment is increased from 0° to 30°.

The asymmetrical flow in the carotid arteries can be seen from TABLE VI in the second volunteer study. The explanation is that the volunteer had no left anterior cerebral artery and no right posterior communicating artery. This can be seen from FIG. 20. FIG. 20 shows not only that the slice selection can correctly be calculated, but also that PCMR flow quantification on current intracranial vessels can be achieved using the 3D localization.

In summary, the 3D localization can be used in cerebral blood flow with PCMR imaging. The technique could prove to be of great value in both evaluating disease and increasing the effectiveness of clinical applications of PCMR imaging. It also becomes possible for the hemodynamic parameters of some curved intracranial vessels in cerebral circulation to be evaluated through the non-invasive PCMR technique.

An empirical study of user variability using the three-dimensional phase contrast MR angiographic flow measurement system was conducted. The study tested the repeatability of measurements by having ten users select the vessel cross-section from the interpolated color velocity images of the cerebrovascular flow. The flow computation performance of the system was verified against the data collected from a constant flow phantom, from ten patients with varying cerebrovascular disease, and from a computational fluid dynamic (CFD) simulation.

The results of the empirical study show that the readings are stable across users, and that the flow measurements show a good degree of fidelity to the flow obtained through clinical measurement and CFD simulation. A 96-percent overall accuracy on 160 measurements was observed for the phantom, with less than 5 percent mean error in the inter-user variability in extraction of the vessel cross-section among the ten users. For the ten patients, the flow computed was satisfactory in qualitative evaluation. The computed flow also correlated very well with those measured with a flowmeter in two patients r=0.985, P<0.001). The flow measurements in the Circle of Willis correlated well with the results of a CFD simulation of two patients (r−10.970, P<0.001).

The surgical treatment of giant aneurysms or head and neck neoplasms often requires permanent occlusion of the internal carotid artery. Tolerance to permanent carotid artery sacrifice is traditionally assessed by temporarily occluding the carotid artery. This procedure is not without risk. The computational model of cerebral circulation of the present invention is a safer alternative to the balloon occlusion test (BOT).

The model used by the system 10 was used to create a virtual replica of the Circle of Willis and compute network blood flow using the finite-difference method. To evaluate the ability of the model to identify patients who tolerate permanent carotid occlusion, the difference in ipsilateral computed middle cerebral artery flow between patients passing and failing the balloon occlusion test was determined prospectively.

Each patient underwent four-vessel angiography and awake temporary occlusion of the internal carotid artery. Failure of the BOT was defined as appearance of any one of the following: a neurological deficit during the BOT, slowing of EEG wave patterns, and a drop in $RSO_2$ of >10 percent.

Five of the 22 patients failed the BOT. The change in computed middle cerebral artery flow was 7+/−0.74 cc/min for patients passing the BOT (p<0.001).

The value of computational fluid dynamics (CFD) in predicting the outcome of BOT is striking. The results suggest a role for CFD in the evaluation of patients for permanent artery occlusion.

The numerical model of the cerebral circulation was utilized along with the data from other supplemental diagnostic modalities to evaluate cerebrocirculatory collateral function during the balloon occlusion test (BOT).

EEG, transcranial Doppler, cerebral oximetry, SPECT, were also done along with the computational modeling for patients undergoing temporary occlusion of the carotid to assess cerebral circulation when permanent occlusion is needed.

Case example: A 49 year old female displayed diplopia and headache. Upon investigation, she was found to have a large right cavernous internal carotid artery (ICA) aneurysm. A computer analysis of her cerebral blood flow was made to assess her cerebral circulation, focusing mainly on the total middle cerebral artery flow. The numerical value of the total middle cerebral artery blood flow with and without occlusion of the ipsilateral ICA was predicted by the computer flow to be almost the same.

| Vessel | Flow computed before balloon occlusion | Flow after balloon occlusion |
|---|---|---|
| Left Middle | 83 | 81 |
| cerebral artery | 40 | 40 |
| and branches | 17 | 16 |
|  | 17 | 16 |
|  | 16 | 17 |
| Total MCA Flow | 169 | 172 |
| Right Middle | 80 | 79 |
| cerebral artery | 38 | 35 |
| and branches | 18 | 17 |
|  | 17 | 17 |
|  | 17 | 15 |
| Total RMCA Flow | 169 | 172 |

In view of the predicted toleration of the occlusion, the patient underwent balloon occlusion of the ICA on the right side, just distal to the aneurysms. The patient displayed good flow in both cerebral hemispheres with minimal changes in total computed middle cerebral artery flow. Concomitantly, there were no change in amplitude in EEG waves, recordings of cerebral oximetry using near infrared spectroscopy, transcranial Doppler (TCD), or clinical deterioration.

Temporary balloon occlusion is invasive and adds risk to the evaluation of patients who may already be at risk for infarction. The numerical model of the cerebral circulation is employed as an aid in the evaluation of patients for permanent internal carotid occlusion.

Pulsatile pressure and flow in normal and diseased vessels (e.g., aneurysms, stenoses) can also be simulated. Modeling of network flow with anatomical variations, bypasses, or lepto-meningeal collateral vessels is also possible.

In this particular case, this model was utilized to simulate changes in the middle cerebral artery blood flow before and after the balloon occlusion. If the blood flow is decreased in a region of the Circle of Willis after occlusion of the carotid artery, the simulation shows red at the region receiving decreased flow, and displays numbers corresponding to the magnitude of the decrease. If the blood flow is increased in a region of the Circle of Willis after occlusion, the simulation shows green at the region receiving increased flow, and denotes the magnitude. From the simulation output, the user can estimate whether the patient will tolerate the occlusion (or would pass the balloon occlusion test).

Under another embodiment of the invention, the modeling system may be extended to sectors of the cerebral vasculature. The generic model results, obtained using the individual patient's vessel sizes (obtained from digital subtraction angiography (DSA)) and a generic pattern of peripheral resistance, indicate satisfactory accuracy for some, but not all, vessel flows. In order to improve the simulation, patient-specific information is needed regarding the peripheral resistance distribution. To achieve this patient-specificity, the flows in certain crucial cerebral arteries must be obtained from phase contrast magnetic resonance angiography (PC-MRA). A patient-specific pattern of resistance can then be calculated. To this end, the original computer program may be modified so that all the efferents to a cerebral sector are melded into one terminal efferent vessel and a measured input flow to that sector is then used to determine its resistance. Seven such sectors have been identified in the cerebral macrovasculature. By combining the sector concept with PCMRA and DSA angiography, enhanced simulations of normal, diseased, and surgeon-modified cerebral configurations have been produced.

Next we provide a generic model. The behavior of the cerebral arterial network with its pulsatile flow occurring in compliant arteries is mimicked using a computer algorithm for unsteady flow in a network of elastic vessels. The primary vessels of the cerebral macrovasculature are included in the network along with a skeleton of vessels, including the heart efferent, to represent the systemic vasculature. It was deemed necessary to include the aorta and subclavians in the simulation because these arteries are the staging vessels where important hemodynamic decisions are made (based on downstream blockage and resistance distributions) as to the delivery of blood into the carotids and vertebrals and the ultimate distribution of blood in the anterior and posterior sections of the circle of Willis. The circle acts as an invaluable distribution center for cerebral blood but the distribution decisions are initiated in the aortic arch and subclavians.

Figure 22:
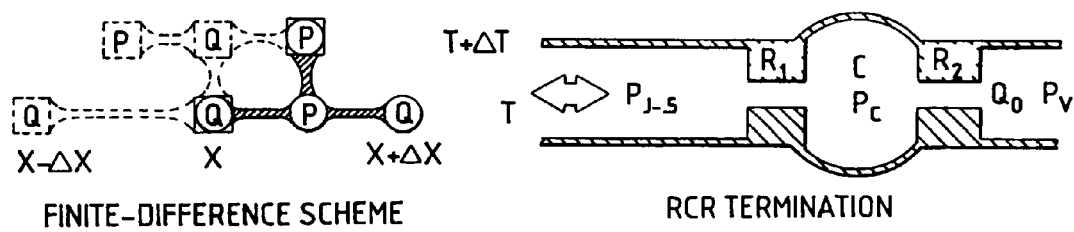
FIG. 22 shows definition sketches of the model used by the system of FIG. 1.

The numeric algorithm that is used to generate the pressures and flows at all locations within the vessel network and at all times during the heart pulse period is a one-dimensional, staggered, explicit finite-difference scheme, based on a conservation of mass relation to calculate the pressures, and a Navier-Stokes momentum equation to calculate the flows. As seen in the cross-hatched portion of the definition sketch below (FIG. 22), the advanced-time pressure can be calculated using the present-time pressure and the present-time spatial gradient of the flow according to the following difference equation:

$$p^{t+\Delta t}_{x+\frac{\Delta x}{2}} = p^{t}_{x+\frac{\Delta x}{2}} - \frac{\Delta t/\Delta x}{(\partial A/\partial P)^t}(Q^t_{x+\Delta x} - Q^t_x) \tag{6}$$

where Q is flow, P pressure, and A cross-sectional area. The compliance is given by the following logarithmic relation attributable to Raines:

$$A(x, P) = A_0(x, P_0)\left[1 + \frac{\beta}{A_0(x, P_0)}\ln\frac{P}{P_0}\right] \tag{7}$$

where β is a constant and subscript 0 refers to initial conditions. The underlying assumption of this relation is that the compliance is inversely proportional to the pressure, i.e., $$\frac{\partial A}{\partial P} = \frac{\beta}{P}.$$

When the flow is in the positive x-direction, the advanced-time flow (see dashed portion of the definition sketch above) can be calculated using the advanced-time spatial pressure gradient, the present-time spatial flow gradient, and the temporal flow gradient according to the following difference equation:

$$\frac{Q_x^{t+\Delta t} - Q_x^t}{\Delta t} + \frac{\Lambda_x^t (Q_x^t)^2 - \Lambda_{x-\Delta x}^t (Q_{x-\Delta x}^t)^2}{A_{x-\frac{\Delta x}{2}}^t} - \frac{\Lambda_x^t Q_x^{t+\Delta t} \Lambda_x^t Q_x^t}{\left(A_{x-\frac{\Delta x}{2}}^t\right)} \left[\frac{A_{x+\frac{\Delta x}{2}}^t - A_{x-\frac{\Delta x}{2}}^t}{\Delta x}\right] =$$

$$-\frac{1}{\rho \Delta x}\left[P_{x+\frac{\Delta x}{2}}^{t+\Delta t} A_{x+\frac{\Delta x}{2}}^t - P_{x-\frac{\Delta x}{2}}^{t+\Delta t} A_{x-\frac{\Delta x}{2}}^t\right] - 2\pi\mu r_1 \frac{\partial \Omega}{\partial r}\bigg|_{r=r_1} Q_x^{t+\Delta t}$$

(8)

where $\Lambda$ and $\Omega$ are momentum and velocity shape factors respectively, and $\rho$, $\mu$ and $r_i$ are blood density, blood viscosity, and vessel inner radius, respectively. The last term of Equation 8, the resistance term, is evaluated using the slope of the velocity profile that is approximated by a sixth-order polynomial.

Not all or even most of the arteries in the cerebral circulation can be included in the model. Some judicious choice must be made as to where to terminate the model. The terminal boundary condition imposed on all efferents of the chosen network is, therefore, most crucial to the flow-distributions predicted by the model and is the main thrust of this effort. A lumped parameter resistance-capacitance-resistance (RCR) combination was used in which the upstream resistance ($R_1$) was set equal to the characteristic impedance of the efferent. This relation when solved for the advanced-time terminal flow takes the following form (refer to RCR definition sketch):

$$Q_j^{t+\Delta t} = \frac{P_{j-0.5}^{t+\Delta t}\left[\frac{C_v}{\Delta t} + \frac{1}{R_2}\right] - \left[(P_{j-0.5}^t - Q_j^t R_1)\frac{C_v}{\Delta t} + \frac{P_v}{R_2}\right]}{1 + R_1\left(\frac{C_v}{\Delta t} + \frac{1}{R_2}\right)}$$

(9)

where $P_{j-0.5}$ and $Q_j$ are the pressure and flow at the inlet of the RCR, $C_v$ is its volume capacitance, $P_v$ is the "venous pressure" at the outlet, $R_1$ and $R_2$ are the resistances.

The forcing function for the model is imposed at the root of the ascending aorta and is in the form of a normal pressure-time diagram there. A set of initial conditions, required to get the numeric process started, is given by setting all nodal pressures equal to the venous pressure and all nodal flows equal to zero. Ten to fifteen pulse periods of calculations are required to bring the pressures and flows into steady-state pulsatility. Computation time for a typical run on a 400 MHz personal computer is approximately three minutes.

Figure 23:
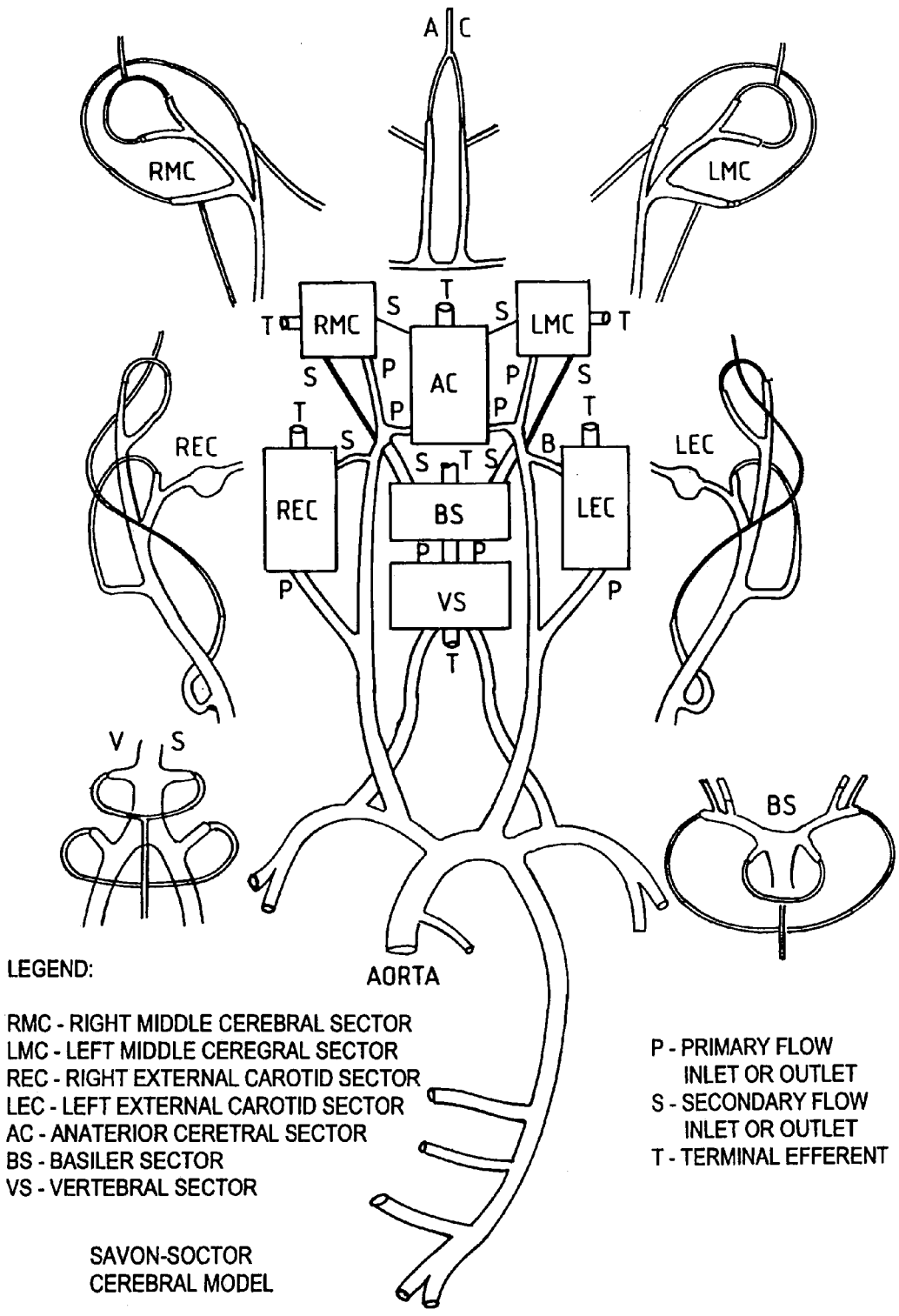
FIG. 23 depicts a seven-sector cerebral model used by the system of FIG. 1.

A sector model may be considered next. With the advent of PCMRA, the non-invasive measurement of cerebral artery flow has become a reality. This advance provided a means by which cerebral circulation simulations could be made more patient-specific. The crucial unknowns in such simulations are the terminal resistances of the modeled vessels. If time in the MRI machine were not a factor, the flow in each individual efferent of the model could be measured and a corresponding resistance could be calculated. To limit machine time and the number of flows to be determined for the patient, a sector model of the cerebral circulation was devised in which all of the terminal vessels in any sector were melded into one terminal vessel. Seven such sectors are shown in FIG. 23 along with the primary and secondary flow inlets and/or outlets and with the terminal efferent for each sector. To determine this one terminal resistance, it is necessary to be able to define the flow into and/or out of the sector.

Figure 21:
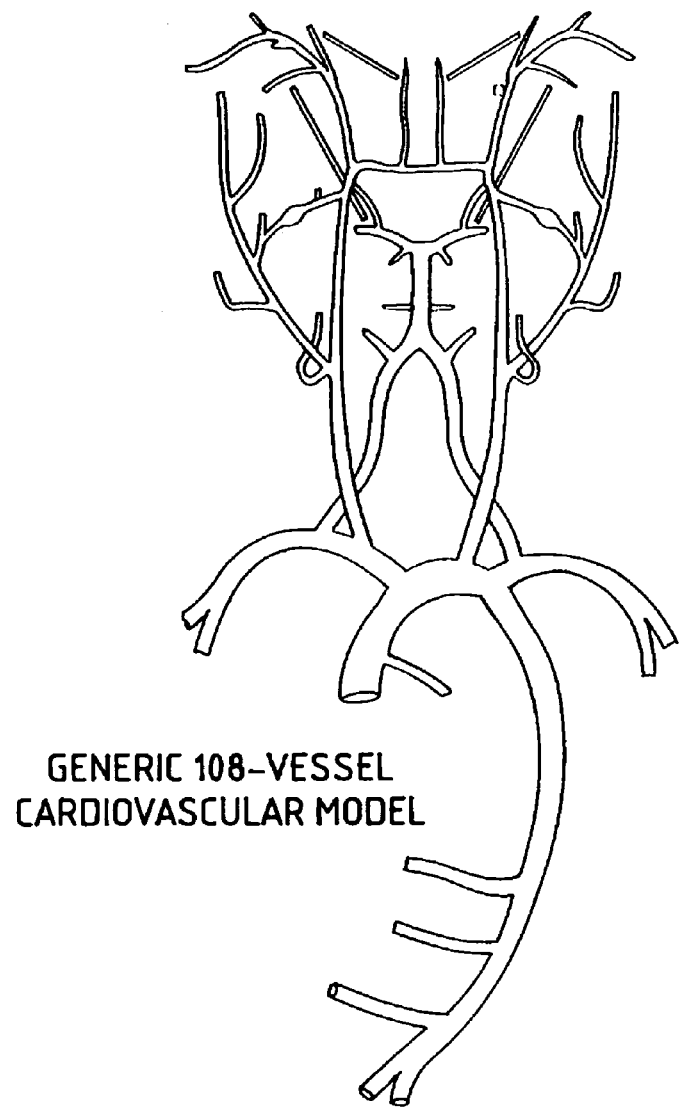
FIG. 21 depicts a generic 108-vessel cardiovascular model used by the system of FIG. 1.

This requirement takes different forms for different sectors. For the left middle cerebral sector (LBC), there are three possible flow inlets (Ml, the main middle cerebral vessel, and two small secondary collaterals or anastomoses) and one terminal resistance efferent. This single efferent takes the place of four efferents used in the original generic model (FIG. 21) and has been formed by melding together these original efferents. The secondary anastomoses are not present in all cases and, when present, it is difficult to measure their flows. Therefore, the M1 flow represents the primary input to this sector and its mean flow value over a pulse period is acquired via PCMRA. The secondary flows are accounted for in the simulation by means of their current calculated values as described below. The right middle cerebral sector (RMC) is handled in a similar manner. In the anterior cerebral sector (AC), there are four possible flow inlets (the left and right anterior cerebral artery A1, and two small secondary collaterals or anastomoses) and one terminal resistance efferent. In the left external carotid sector (LEC), there are two possible flow inlets (the left external carotid artery and the left ophthalmic artery) and one terminal resistance efferent. The right external carotid sector (REC) is treated similarly. In the basilar sector (BS), there are five possible flow inlets (the downstream segment of the basilar itself, the two posterior communicating arteries, and two small collaterals) and one terminal efferent (resulting from the melding of the two posterior cerebral arteries and two superior cerebellar arteries). The basilar flow is the primary input to this sector and again it must be determined using PCMRA. The other four secondary vessels can be either inflow and/or outflow vessels depending on the overall resistance balance in the system. The four secondary contributions are accounted for in the simulation by using their current calculated values. In the vertebral sector (VS), there are three possible flow inlets (the left and right vertebral artery, and the downstream segment of the basilar) and one terminal resistance efferent. All three flows must be determined by PCMRA.

Figure 24:
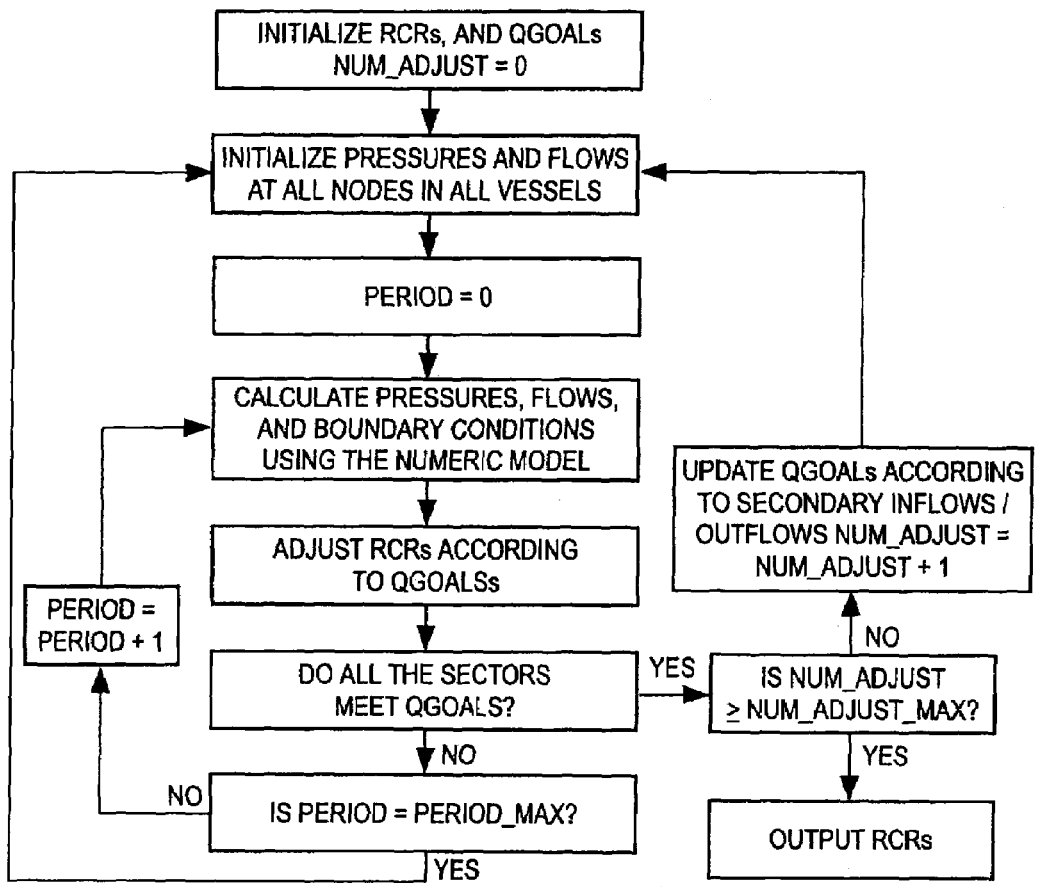
FIG. 24 is a flow chart of the sector model used by the system of FIG. 1.
Figure 30:
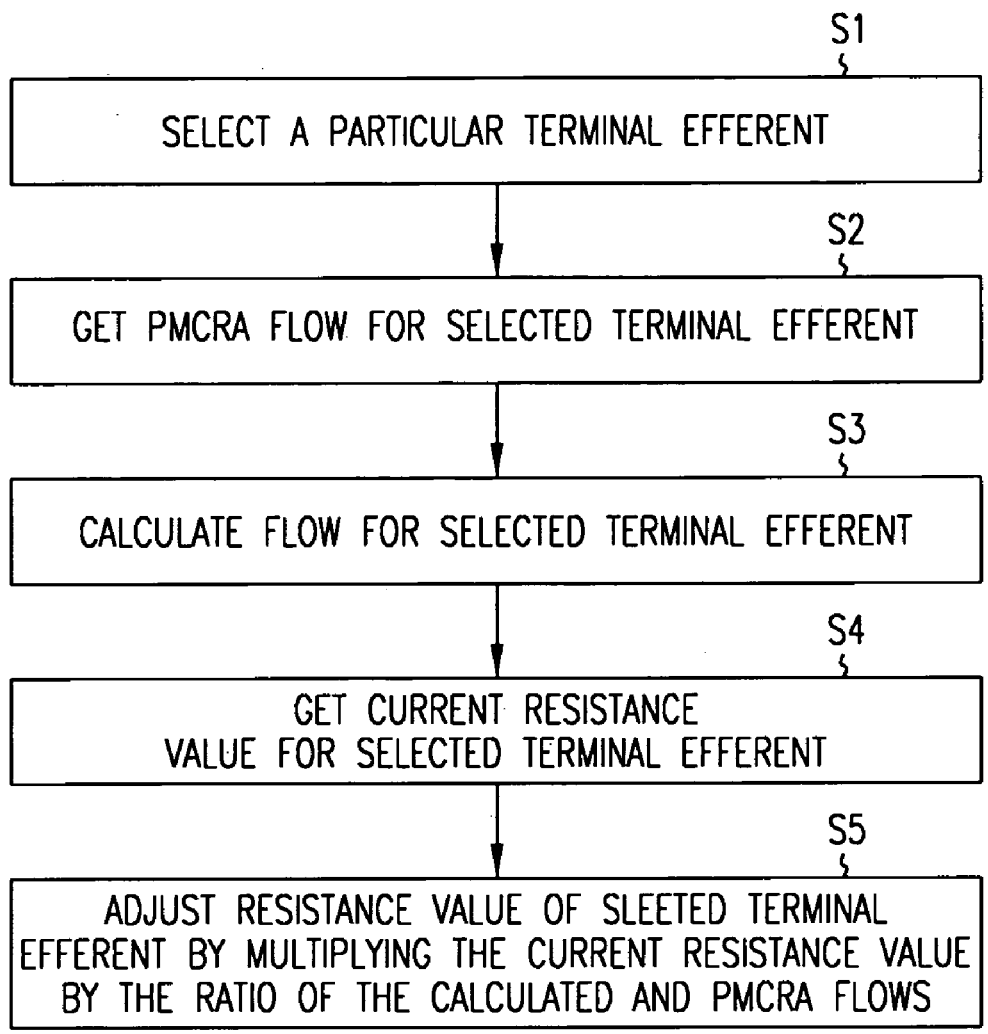
FIG. 30 illustrates an exemplary procedure for adjusting a sector terminal efferent resistance.

To start the computations for the sector model (FIG. 24), the assumption is made that the flow (QGOAL in FIG. 24) in the terminal efferent for the sector is the same as the PCMRA measured flow in the primary input flow vessel, ignoring, for this first set of calculations, the other secondary inflows or outflows. A plausible set of terminal resistances are needed to start the calculations and be concocted either from a steady flow model of the vessel system or from a previous similar simulation. After each (pulse) period of calculation, the program adjusts the resistance for each sector terminal efferent by multiplying its current resistance by the ratio of the current calculated terminal flow to the goal (PCMRA) flow for that terminal. An exemplary procedure for adjusting the resistance of a sector terminal efferent is illustrated as steps S1 through S5 in FIG. 30. This procedure would correctly adjust any one terminal flow but, since all the other terminal resistances are adjusted concurrently, errors are introduced and many adjustments are needed in subsequent periods. This process continues for up to a user-specified number of pulse period of calculations period-max in FIG. 24. A check is made at the end of each period to see if the measured sector flow goal has been achieved by the adjustment of the resistance of the terminal efferent. If all seven sector flow goals are achieved within in the period limit, the program proceeds to the next step. If the goals are not met after the maximum number of periods, the program starts over with the current efferent resistances and the original initial conditions of zero flow and venous pressure at all nodes in all vessels.

The next step in the procedure is the adjustment of the flow goals (QGOALs in FIG. 24) so as to account for the secondary inflows and/or outflows. Since all vessels in the model are involved in the calculations discussed above, the secondary flows have been continually updated in this process. In this set of calculations, the flow in the terminal efferent is set equal to the primary PCMRA flow adjusted for the flows in the secondary inlets and/or outlets. For the left middle cerebral sector, this amounts to adjusting the M1 flow for the inflow or outflow contributions of the two secondary anastomoses. For the basilar sector, the contributions of the posterior communicating arteries and the two secondary anastomoses must be considered with proper signs. For the left external carotid sector, the ophthalmic flow must be combined with the left external carotid PCMRA flow in subsequent calculations. These adjustments are made only at the beginning of a period_max run, which can be cut short if all sector flow goals are met. When a user-specified number of adjustments have been made, the program ends.

At this stage of the simulation, a patient-specific set of resistances has been generated from patient DSA angiograms and measured PCMRA sector flows. This resistance pattern can now be assumed to be invariant in additional simulations of this patient. Modifications in system configuration can be made, say, by inserting a bypass vessel between the external and internal carotid arteries or by vessel occlusion in the treatment of an aneurysm. The neurosurgeon can now play "what if?" games with the computer program to plan the best strategies for his/her treatment of the patient.

Cerebral blood flow quantification may be considered next. Flow quantification with PCMRA provides a powerful tool to non-invasively analyze blood flow. It has been shown to do well in assessing both in vitro and in vivo flow velocities and volumetric flow rates. The inaccuracies of both velocity and VFR in vitro measurements in large vessels are about 5–10 percent under continuous and pulsatile flow conditions.

Blood flow measurements are influenced by many MR parameters: among these is the orientation of the vessel relative to the scan plane. The MR data acquisition is sensitive to any flow along the through-plane axis. If the through-plane axis is not parallel to the flux through the vessel, only a component of the true velocity is detected. This situation can arise when the imaging plane is not perpendicular to the vessel of interest. Wedding studied the effects of misalignment in vitro.

A three-dimensional (3D) localization algorithm has been developed by Zhao et al. for the determination of slice selections that are perpendicular to the flow directions for cerebral vessels during scanning and the identification of cerebral vessels from PCMRA images with oblique scans during post-processing. The 3D localization of slice selection was developed based on a 1.5 Tesla MRI General Electric imager. A 3D time of flight MRA covering the circle of Willis is performed and the images are extracted and transferred to a SGI workstation. The 3D surface rendering of the vasculature is then reconstructed from these images using a Marching-Cube algorithm. The coordinates obtained from the 3D localization based on the 3D surface rendering specify the position of an oblique cine PCMRA scan. A cine PCMRA is then performed based on those coordinates. The following parameters were used: TR, 33 ms; TE, minimum; flip angle, 30; number of excitations, 2; field of view, 16 cm; image matrix, 256×128; number of phases, 32; slice thickness and velocity encoding (VENC) are 5 mm and 100 cm/sec for carotids, VA, and BA, and 4 mm and 70 cm/sec for MCA and ACA. The vessel area is semi-automatically determined through an interface on a SGI workstation. The velocity and volumetric flow rate (VFR) can then be calculated over the time course of the pulse period.

This algorithm provides for the determination of cerebral blood flow in eleven major cerebral arteries from PCMRA (left and right CCA, left and right VA, left and right ICA, left and right MCA, left and right ACA, and BA). The mean values of the VFRs from these eleven vessels provided the primary inlet/outlet flows used in the sector model. The MR scan time is about an hour per patient.

Following is a presentation of results and case studies. To exhibit the efficacy and abilities of the sector model of the cerebral circulation, three cases relating to the balloon occlusion test (BOT) used in the treatment of non-operable cerebral aneurysms will be presented and discussed. When an aneurysm is to be treated by occluding the vessel to which it is attached, a temporary occlusion of the vessel is made with a balloon to test the clinical outcome of the patient to permanent occlusion. Since the BOT is not without risk, the patient would benefit if a BOT computer simulation could be substituted. The three cases presented for discussion are intended to show how well the model predicts the BOT outcome.

Case 1. A 51-year-old white male presented with a two-month's history of progressively worsening left pulsatile tinnitus. Angiogram and PCMRA studies showed that both the left and right posterior communicating arteries and the A1 segment of the left anterior cerebral artery were small. The left internal carotid artery contained a large aneurysm and a stenosis of 60 percent. These data were used as Baseline in the computer simulation. The patient subsequently passed a BOT. A permanent occlusion of the LICA was made with balloons trapping the diseased distal cervical segment of the LICA.

Case 2. A 56-year-old black female presented with a subarachnoid hemorrhage. Angiogram and PCMRA studies showed multiple aneurysms including a giant aneurysm at the left superior hypophyseal artery as well as a 40 percent stenosis in the left internal carotid artery. The patient failed the BOT under hypotensive challenge, becoming hemiparetic and aphasic during the test. SPECT also showed a massive difference between the two hemispheres with a significant decreased relative blood flow in the left hemisphere involving the frontoparietal, occipital and temporal lobes. A PCMRA CBF study was performed before the BOT. These data were used in the Baseline simulation.

Case 3. A 71-year-old white female presented with persistent headache. Angiogram and PCMRA studies showed a large right carotid-ophthalmic aneurysm as well as occlusions of both left and right posterior communicating arteries, occlusion of the anterior communicating artery, and a 40 percent stenosis in the left anterior cerebral artery. These data were considered as the Baseline in the computer simulation. A PCMRA CBF study was performed before the BOT. During the BOT in the right internal carotid artery, an immediate failure ensued when left side hemiparesis developed.

Figure 25A:
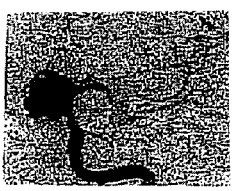
FIG. 25 depicts an angiogram, 3D localizer image and flow waveform of a patient provided by the system of FIG. 1.
Figure 25B:
Figure 25C:
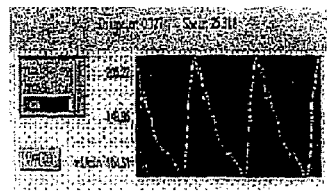
Figure 26A:
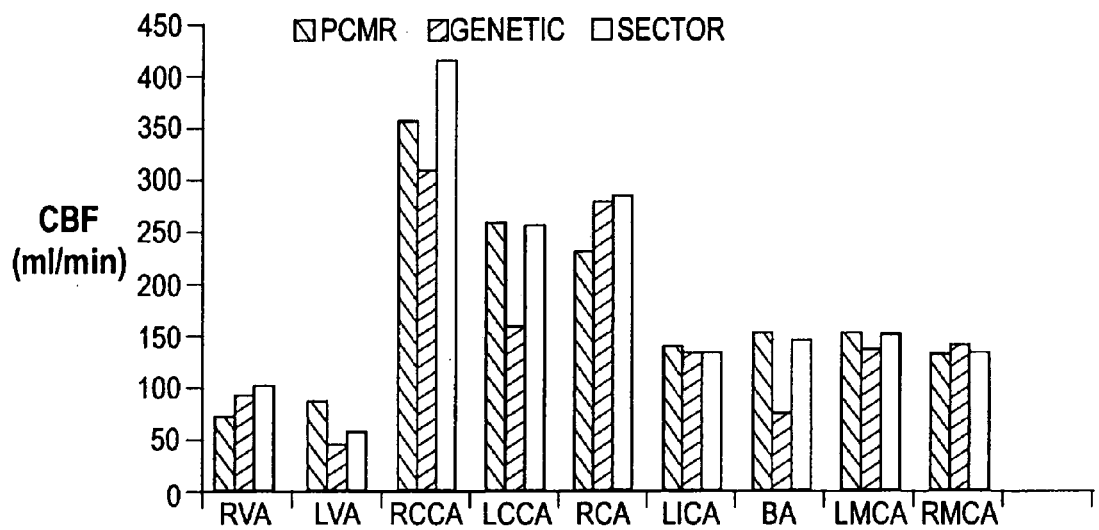
FIG. 26 depicts case results produced by the system of FIG. 1.
Figure 26B:
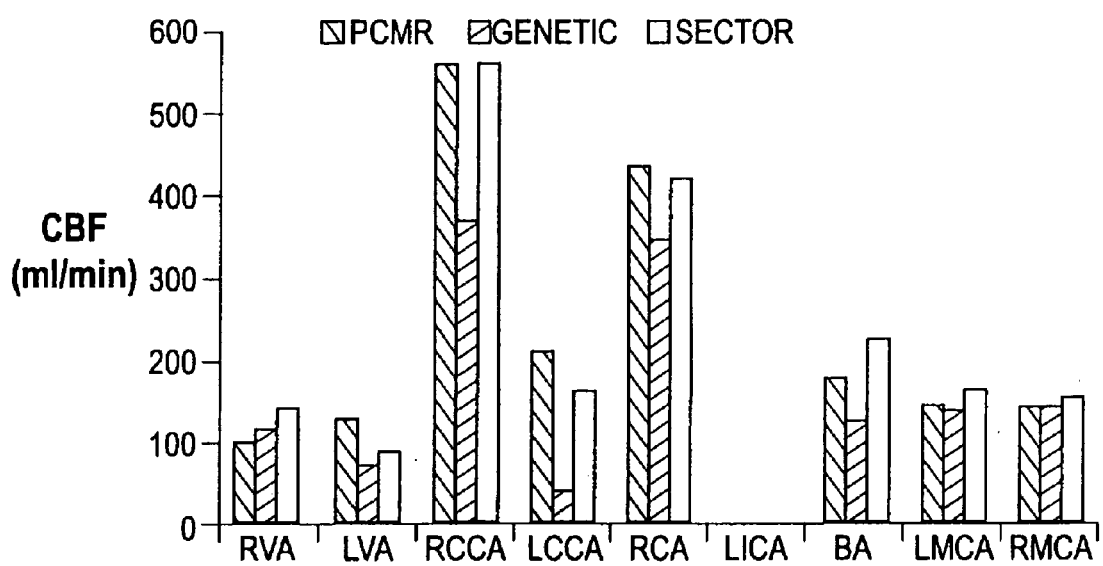
Figure 26C:
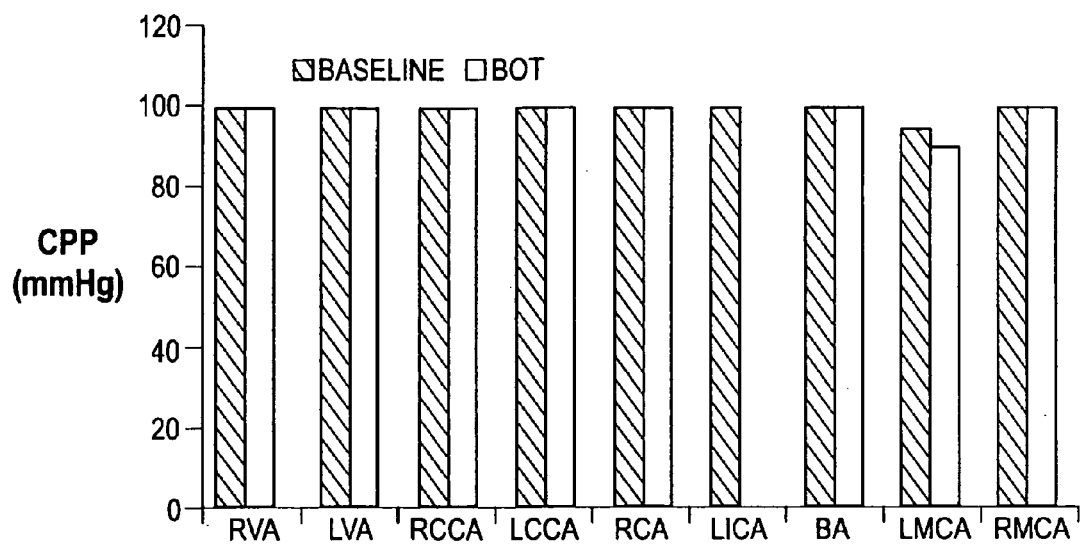
Figure 26D:
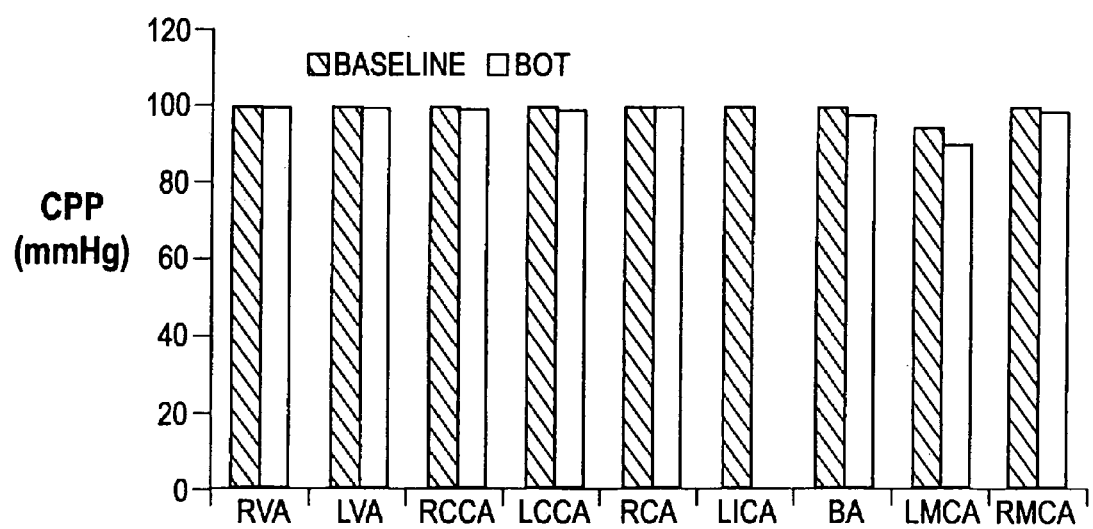

A typical angiogram, 3D localizer image, and flow waveform are presented in FIG. 25. The PCMRA and simulation results are shown in the form of bar graphs in FIG. 26 for Case 1 and in FIG. 27 for Cases 2 and 3. A typical set of simulation results is shown in both numeric and color forms for Case 2 in FIG. 28. These results will be discussed in detail in the next section.

The purpose of this discussion is to demonstrate the efficacy of a novel simulation technique, the sector model, in the patient-specific prediction of clinical outcomes accompanying surgical intervention. The specific intervention considered here is the treatment of inoperable aneurysms by permanent occlusion of a carotid artery. The patient's tolerance of such an occlusion is determined by temporarily occluding the artery, the balloon occlusion test (BOT). Since this test is not without risk, it would be beneficial for the patient to substitute a valid computer simulation for it.

The PCMRA flow measurements along with the sector and generic model results are displayed in FIGS. 26 and 27. For case 1, the Baseline results in FIG. 26a show excellent agreement between the PCMRA flow and the sector model results for most vessels. This result was expected since the PCMRA flow measurements were used in the RCR adjustments to satisfy the iterative process of FIG. 24. Once the RCR pattern had been determined for this patient, it was used independently to predict the post-BOT results shown in FIG. 26b. Here again, the agreement between the PCMRA and the sector model results is excellent (with the possible exception of the LVA). The generic model compared well with the PCMRA measurements for some vessels, but not as consistently as the sector model. For cerebral perfusion pressure (CPP) results in FIGS. 26c and 26d, both sector and generic models give comparable predictions for Baseline and BOT with no dramatic pressure drops during the test. Since the patient passed the test, these results are also compatible with the clinical outcome.

Figure 27A:
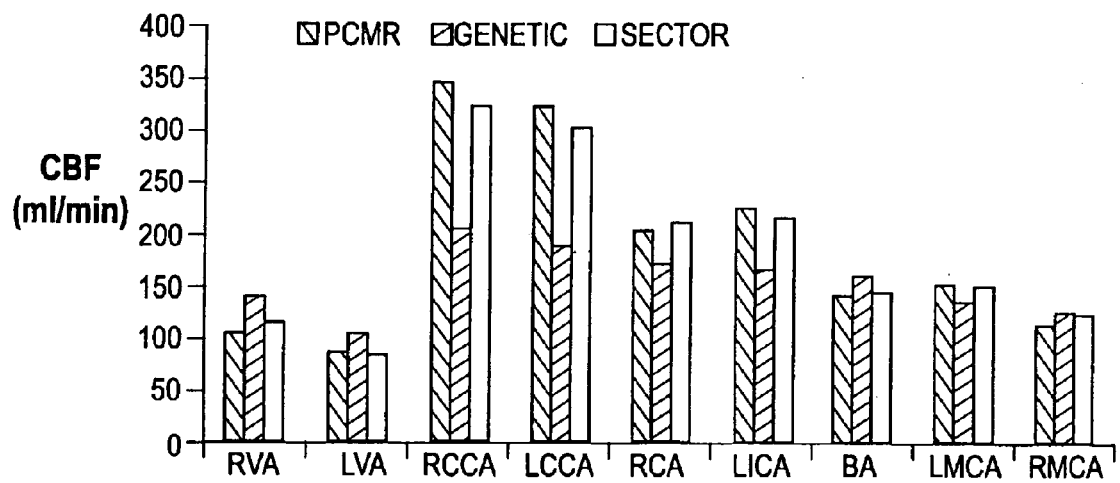
FIG. 27 depicts further case results produced by the system of FIG. 1.
Figure 27B:
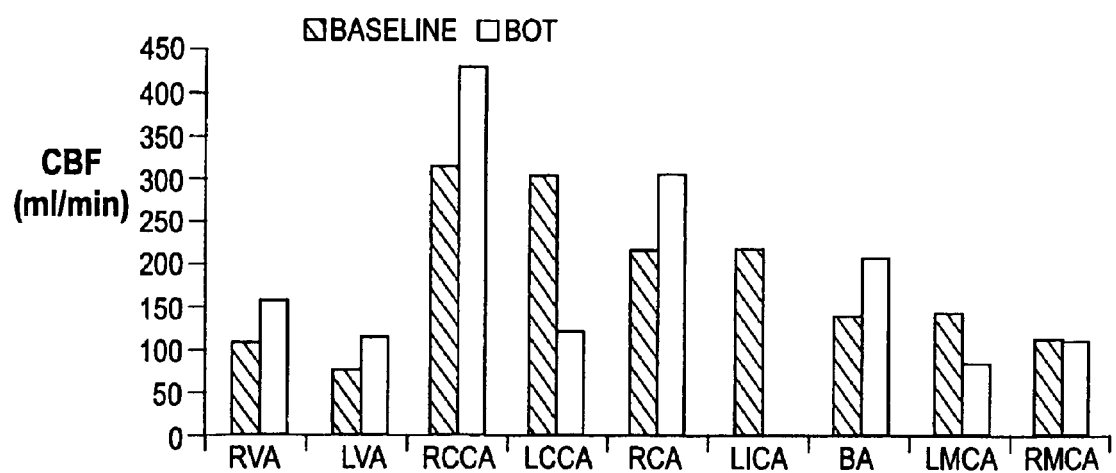
Figure 27C:
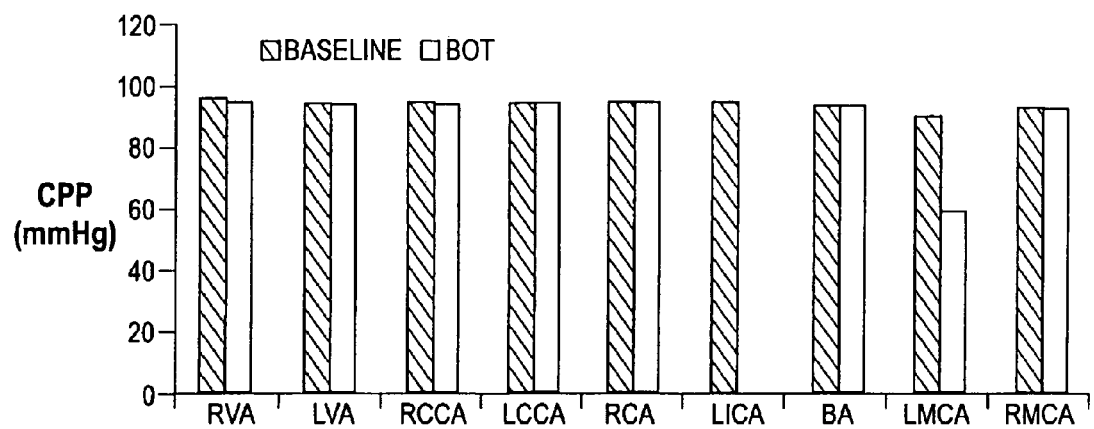
Figure 27D:
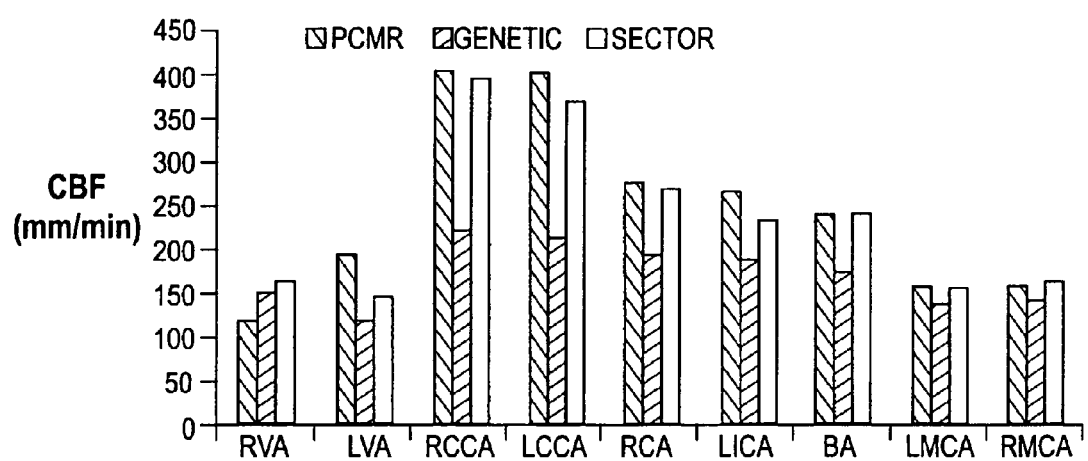
Figure 27E:
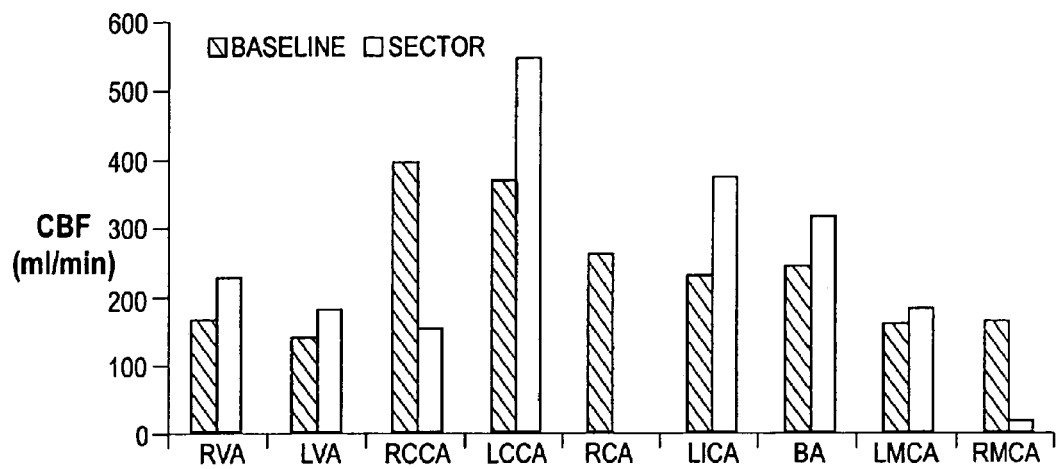
Figure 27F:
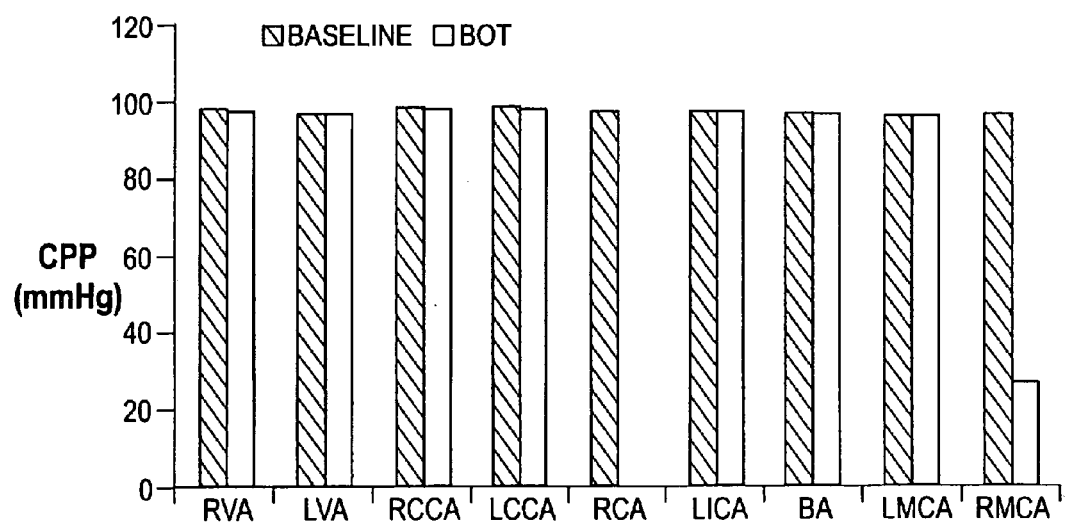

Similar results were obtained for Cases 2 and 3 for Baseline CBF as shown in FIGS. 27a and 27d. Since both patients failed the BOT test, there are no post-BOT PCMRA data to compare with the simulation results. Therefore, only calculated Baseline and BOT CBF values are shown in FIGS. 27b and 27c for Cases 2 and 3, respectively. These cases have drastically different flow patterns in the carotid vessels (RCCA, LCCA, RICA, LICA) because of the balloon closure of the LICA and RICA in Cases 2 and 3, respectively. For the BOT simulation, the reduction in flow values for the LMCA in Case 2 and the RMCA for Case 3 in comparison with the Baseline values is compatible with the clinical outcome of BOT failure. A similar result for CPP values for these arteries is shown in FIGS. 27c and 27f. The reduction in flow and pressure for Case 2 was not as pronounced as that for Case 3 because Case 2 failed the BOT only under hypotensive challenge. In Case 3, the reduction in flow is nearly 100 percent and the pressure is reduced to venous pressure levels in the RMCA.

For Case 3, when the seven-sector model was used to simulate the BOT, an anomaly was discovered in the AC sector. All possible inflow paths to the RMC and AC sectors were seemingly blocked by the occlusions indicated in Section 5. However, the sector model found the one unblocked path. That path started by following the LAC up to the junction of the terminal efferent. Since only part of the available LAC flow was needed to satisfy that efferent, the rest passed down the RAC and went on to satisfy the RMC sector. To correct this implausible solution and to prevent the anomaly, an eight-sector model was used with two separate AC sectors. However, the resulting RAC and RMC sectors had no connection to the forcing function in the ascending aorta except for minor contributions from the small ophthalmic and two secondary anastomoses. the results of the new simulation showed essentially zero flow and venous pressure levels in these sectors. The immediate left side hemiparesis in this patient is subsequently explained by these simulation results.

Figure 28A:
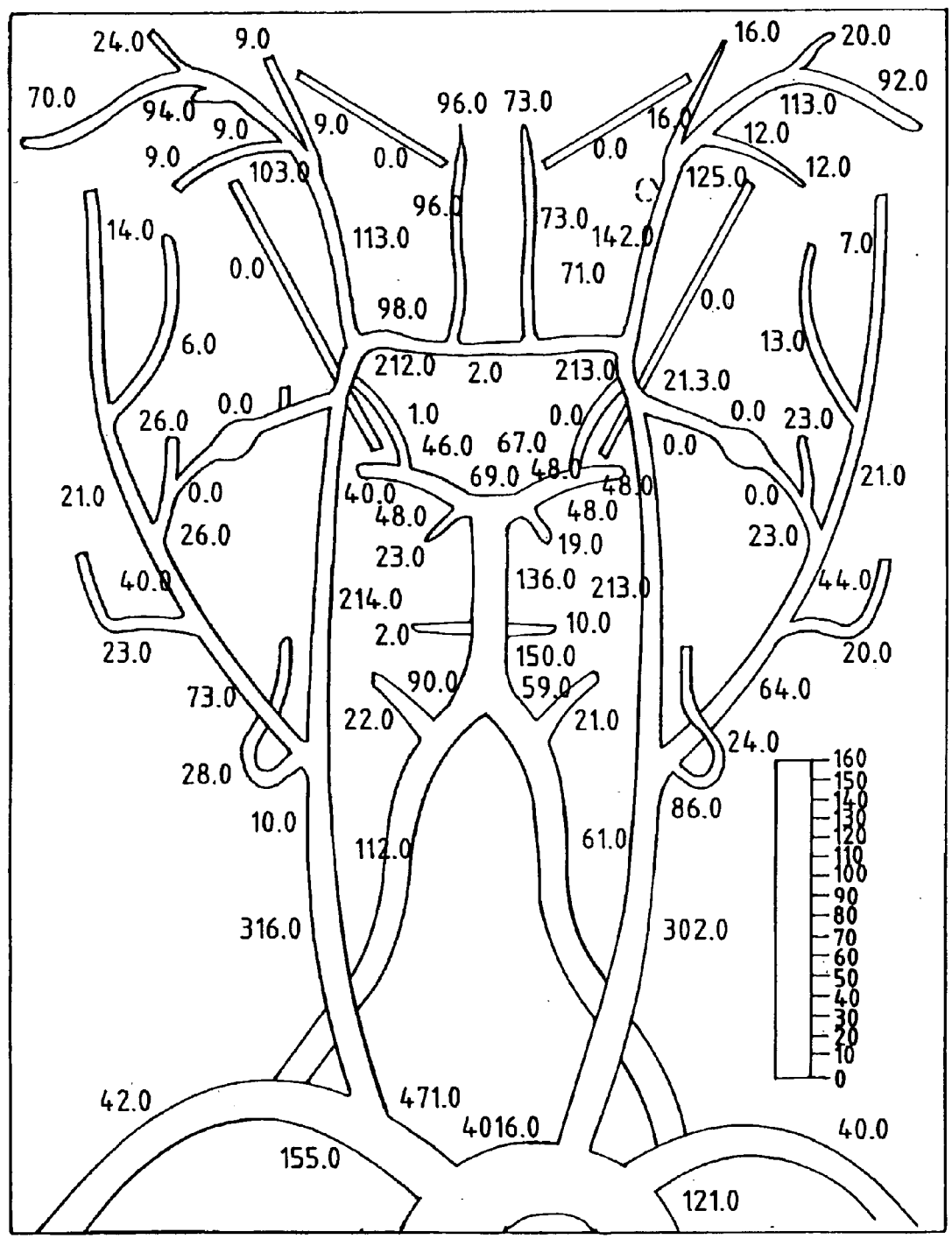
FIG. 28 depicts simulated CBF distributions and BOT of Case 2 performed by the system of FIG. 1.
Figure 28B:
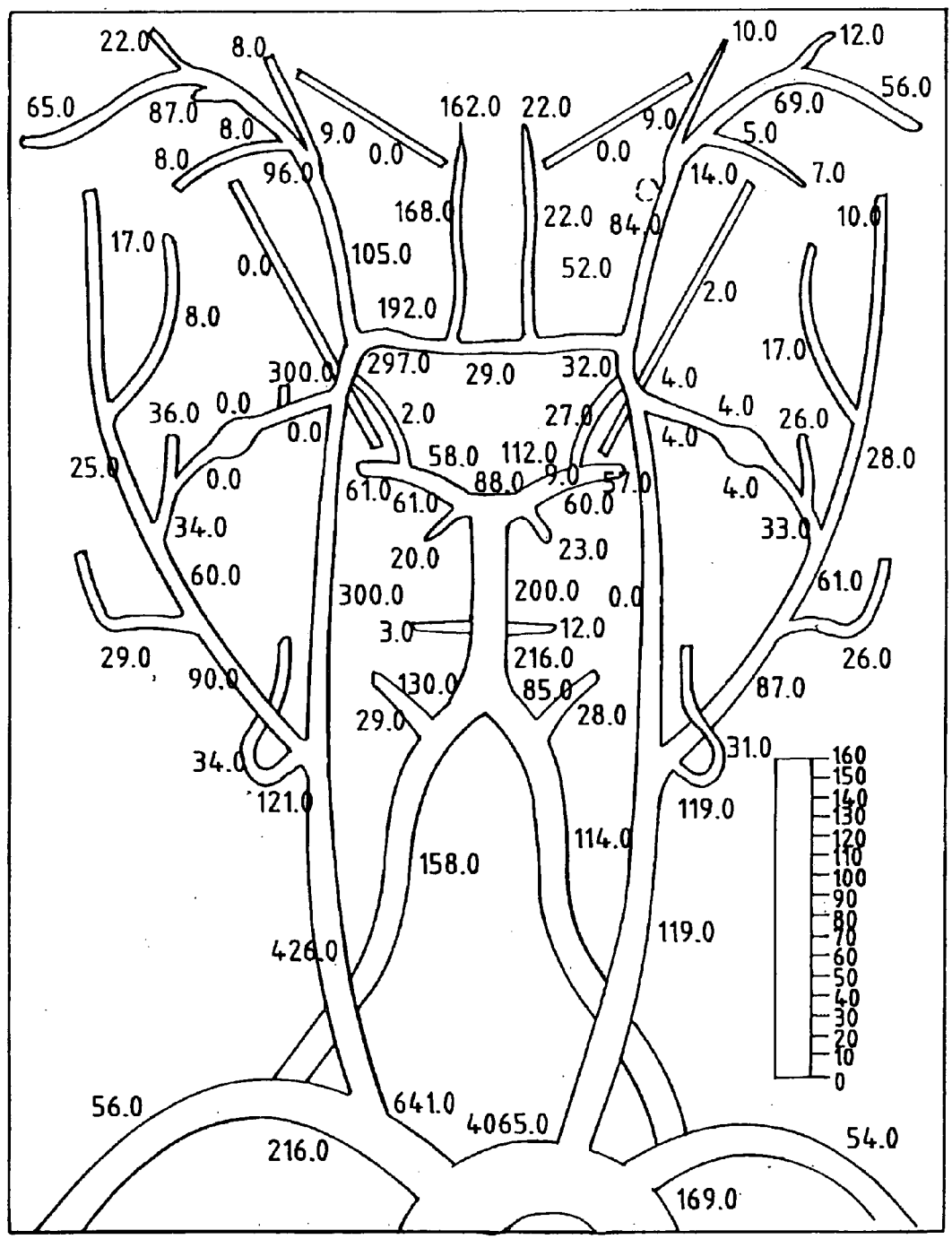

An alternative method of presenting the simulation results is shown in FIG. 28 where the arterial network is depicted with the various arteries colorized (gray scales in printed version) in accord with the amount of flow in them. The actual flow values are also provided along side of the artery. The color coding agrees with that used in other modalities such as SPECT in order to provide the surgeon with an overall visual understanding of the flow changes resulting from a surgical intervention, in this case a carotid occlusion during BOT.

In conclusion, patient-specificity has been achieved in the simulation and analysis of the three BOT patients. These results demonstrate a significant advance in computer modeling of the cerebral circulation through the introduction of the sector model. While the present study only examined three cases, the results clearly demonstrate the working hypothesis of this sector model. Many improvements are envisioned for future models: the forcing function can be made more patient-specific; the systemic portions of the model can be made into sectors and governed by PCMRA measurements; and the autoregulatory aspects of the cerebral arterioles can be added to the simulation. In addition, the model can be generalized to other regions of the cardiovascular system like the coronary circulation or the circulation in the extremities. A model that can accurately predict cerebral blood flow will provide an invaluable tool for physicians in managing complex cerebral problems.

The evolution of models of the cerebral circulation has paralleled the progress in the fields of fluid dynamics and computer science. With each new possibility of simulation, a closer approach to "physiological" modeling was achieved. The ideal model would be patient specific, highly predictive, and reflective of actual conditions both at the macro and micro circulation level. In addition, such an ideal model would be easily re-configurable to conform with the "real time" demands of clinical medicine.

Although computer models of various degrees of sophistication have been proposed to simulate the cerebral circulation, they have been used mainly as theoretical and research tools. Turning them into tools for clinical applications has the potentially powerful benefit of predicting the result of neurovascular reconstructive procedures. However, none of the published models has ever been validated in vivo using quantitative human data, partly because of the lack of available tools for measuring such data.

The method described above offers significant benefit, not only for stroke victims, but also for victims of trauma or congenital circulatory problems. The model has also been developed for other parts of the body such as the heart, extremities, etc. Also it may have application to forensic uses. In any application, it is believed that the model offers significant benefits in helping to understand the effects of potential treatment options available to the physician.

A specific embodiment of a method and apparatus for modeling cerebral circulation according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

The invention claimed is:

1. A method of modeling circulation in a living subject, such method comprising the steps of:
    simulating the fluid dynamics of an arterial network, wherein the simulation models blood flow through a plurality of arterial segments including one or more terminal efferent vessels;
    adapting the simulation to substantially conform to a specific arterial anatomy of the living subject;
    forcing the simulation with a forcing function made up of one or more flow-time or pressure-time signatures;
    calculating a blood flows in the arterial network based upon the forced simulation;
    measuring a blood flow in the living subject;
    correcting the simulation based on the measured and calculated blood flows;
    modifying the simulation to model a particular interventional procedure; and,
    calculating a post-procedure blood flow in a selected arterial segment using the modified simulation in order to predict an outcome of the actual interventional procedure performed in the living subject.

2. The method of modeling as in claim 1 wherein the simulated arterial network includes the Circle of Willis.

3. The method of modeling as in claim 1 wherein the step of adapting the simulation to substantially conform to the living subject's anatomy further comprises conforming a vessel of the simulation with a corresponding vessel in an image of the living subject.

4. The method of modeling as in claim 3 wherein the step of adapting the simulation to substantially conform to the living subject's anatomy further comprises measuring a diameter of the corresponding vessel in the image of the living subject.

5. The method of modeling as in claim 4 further comprising localizing the corresponding vessel in three-dimensional space and tracing a boundary into adjacent areas in three-dimensional space to locate respective ends of the corresponding vessel.

6. The method of modeling as in claim 1 wherein the simulation of the arterial network includes a one-dimensional, explicit, finite difference algorithm based upon a conservation of mass equation, a Navier-Stokes momentum equation, and an equation of state relating local pressure to local artery size.

7. The method of modeling as in claim 1 wherein the simulation is forced with a flow measurement obtained from the living subject.

8. The method of modeling as in claim 1 wherein the simulation is forced with a pressure-time signature obtained from a prototypical measurement.

9. Apparatus for modeling circulation within a living subject, such apparatus comprising:
    a computerized model of an arterial network made up of a plurality of arterial segments including one or more terminal efferent vessels, wherein the apparatus includes means for calculating blood flows in the arterial network when the model is forced with a forcing function;
    means for adapting the model of the arterial network to substantially conform to a specific arterial anatomy of the living subject;
    means for measuring a blood flow in the living subject;
    means for correcting the model based upon the calculated and measured flows;
    means for modifying the model to reflect a particular interventional procedure; and,
    means for calculating a post-procedure blood flow in a selected arterial segment using the modified model in order to predict an outcome of the actual interventional procedure performed in the living subject.

10. The apparatus for modeling as in claim 9 wherein the circulation model further comprises the Circle of Willis.

11. The apparatus for modeling as in claim 9 wherein the means for measuring blood flow is a phase contrast magnetic resonance angiography flow measurement system.

12. The apparatus for modeling as in claim 11 wherein the means for adapting the model to substantially conform to the living subject's anatomy further comprises means for selecting a vessel of the model and a corresponding vessel in an image of the living subject.

13. The apparatus for modeling as in claim 12 wherein the means for adapting the model to substantially conform to the living subject's anatomy further comprises means for measuring a diameter of the corresponding vessel.

14. The apparatus for modeling as in claim 13 further comprising means for localizing the corresponding vessel in three-dimensional space and tracing a boundary into adjacent areas in three-dimensional space to locate respective ends of the corresponding vessel.

15. The apparatus for modeling as in claim 9 wherein the computerized simulation model includes a one-dimensional, explicit, finite difference algorithm based upon a conservation of mass equation, a Navier-Stokes momentum equation, and an equation of state relating local pressure to local artery size.

16. The apparatus for modeling as in claim 9 wherein the model is forced with a flow measurement obtained from the living subject.

17. The apparatus for modeling as in claim 9 wherein the model is forced with a pressure-time signature obtained from a prototypical measurement.

18. The method of claim 1 further comprising the step of obtaining a flow measurement in the living subject by phase contrast magnetic resonance angiography.

19. The method of claim 1 further comprising the step of obtaining a flow measurement in the living subject by a Doppler flow measurement.

20. The apparatus for modeling as in claim 9 wherein the means for measuring blood flow is a Doppler flow measurement device.

21. The method of claim 1 wherein the arterial network is divided into a plurality of sectors, wherein each sector is terminated by a terminal efferent vessel and has a primary input vessel, and further wherein the terminal efferent vessels are modeled as terminal efferent resistances, the method further comprising:
    (a) measuring blood flows in the living subject corresponding to the primary input flows of the sectors;
    (b) adjusting the terminal efferent resistances for each sector in a manner which tends to make the calculated flow in the terminal efferent vessel match the measured primary input flow for each such sector.

22. The method of claim 21 further comprising repeating the calculation of blood flows in the terminal efferent vessels and adjustment of terminal efferent resistances a selected number of times.

23. The method of claim 21 further comprising repeating the calculation of blood flows in the terminal efferent vessels and adjustment of terminal efferent resistances until the differences between the calculated terminal efferent flows and the corresponding measured primary input flows for each sector are within specified limit values.

24. The method of claim 21 wherein the terminal efferent resistance of a sector is adjusted by multiplying the terminal efferent resistance by the ratio of the measured primary input flow to the calculated terminal efferent flow.

25. The method of claim 21 wherein one or more sectors has one or more secondary input or output vessels and further comprising:
- calculating flows through the secondary input and output vessels; and,
- adjusting the terminal efferent resistances for each sector in a manner which tends to make the calculated flow in the terminal efferent vessel match the measured primary input flow adjusted for the calculated flows in the secondary input and output vessels.

26. A system for modeling circulation within a living subject, comprising:
- a computerized model of an arterial network made up of a plurality of arterial segments including one or more terminal efferent vessels, wherein the system includes means for calculating blood flows in the arterial network when the model is forced with a forcing function;
- means for adapting the model of the arterial network to substantially conform to a specific arterial anatomy of the living subject;
- wherein the arterial network is divided into a plurality of sectors, wherein each sector is terminated by a terminal efferent vessel and has a primary input vessel, and further wherein the terminal efferent vessels are modeled as terminal efferent resistances;
- means for measuring blood flows in the living subject corresponding to the primary input flows of the sectors; and
- means for adjusting the terminal efferent resistances for each sector in a manner which tends to make the calculated flow in the terminal efferent vessel match the measured primary input flow for each such sector.

27. The system of claim 26 further comprising means for iteratively calculating blood flows in the terminal efferent vessel of each sector and adjusting the terminal efferent resistances for each sector in a manner which tends to make the calculated flow in the terminal efferent vessel match the measured primary input flow for each such sector.

28. The system of claim 26 further comprising means for iteratively calculating blood flows in the terminal efferent vessel of each sector and adjusting the terminal efferent resistances for each sector in a manner which tends to make the calculated flow in the terminal efferent vessel match the measured primary input flow for each such sector until the differences between the calculated terminal efferent flows and the corresponding measured primary input flows for each sector are within specified limit values.

29. The system of claim 26 wherein the terminal efferent resistance of a sector is adjusted by multiplying the terminal efferent resistance by the ratio of the measured primary input flow to the calculated terminal efferent flow.

30. The system of claim 26 wherein one or more sectors has one or more secondary input or output vessels and further comprising:
- means for calculating flows through the secondary input and output vessels; and,
- means for adjusting the terminal efferent resistances for each sector in a manner which tends to make the calculated flow in the terminal efferent vessel match the measured primary input flow adjusted for the calculated flows in the secondary input and output vessels.

* * * * *